(12) United States Patent
Cha et al.

(10) Patent No.: US 9,353,119 B2
(45) Date of Patent: May 31, 2016

(54) COMPOSITION FOR PREVENTING AND TREATING NON-SMALL CELL LUNG CANCER, CONTAINING PYRAZINO-TRIAZINE DERIVATIVES

(75) Inventors: Joo-Young Cha, Gyeonggi-do (KR); Kwan-Hoo Lee, Gyeonggi-do (KR); Ji-Eun Jung, Seoul (KR)

(73) Assignee: JW PHARMACEUTICAL CORPORATION, Seoul (KR)

( * ) Notice: Subject to any disclaimer, the term of this patent is extended or adjusted under 35 U.S.C. 154(b) by 0 days.

(21) Appl. No.: 14/237,641

(22) PCT Filed: Aug. 7, 2012

(86) PCT No.: PCT/KR2012/006260
§ 371 (c)(1),
(2), (4) Date: Feb. 7, 2014

(87) PCT Pub. No.: WO2013/022257
PCT Pub. Date: Feb. 14, 2013

(65) Prior Publication Data
US 2014/0235581 A1    Aug. 21, 2014

Related U.S. Application Data

(60) Provisional application No. 61/555,428, filed on Nov. 3, 2011.

(30) Foreign Application Priority Data

Aug. 9, 2011    (KR) ........................ 10-2011-0079314

(51) Int. Cl.
| | | |
|---|---|---|
| C07D 487/04 | (2006.01) | |
| C07D 403/04 | (2006.01) | |
| C07D 403/06 | (2006.01) | |
| C07D 403/14 | (2006.01) | |
| C07D 401/14 | (2006.01) | |
| A61K 31/53 | (2006.01) | |
| A61P 35/00 | (2006.01) | |
| C07F 9/6561 | (2006.01) | |

(52) U.S. Cl.
CPC .............. *C07D 487/04* (2013.01); *A61K 31/53* (2013.01); *C07F 9/6561* (2013.01)

(58) Field of Classification Search
CPC .. C07D 487/04; C07D 403/04; C07D 403/06; C07D 403/14; C07D 401/14; A61K 31/53
USPC .......................................... 544/184; 514/243
See application file for complete search history.

(56) References Cited

U.S. PATENT DOCUMENTS

| | | | | |
|---|---|---|---|---|
| 7,232,822 B2 * | 6/2007 | Moon et al. | ........... | 514/243 |
| 7,566,711 B2 * | 7/2009 | Moon et al. | ........... | 514/243 |
| 7,576,084 B2 * | 8/2009 | Moon et al. | ........... | 514/243 |
| 7,585,562 B2 * | 9/2009 | Hasui et al. | ........... | 428/378 |
| 7,585,862 B2 | 9/2009 | Moon et al. | ........... | 514/249 |
| 7,671,054 B1 * | 3/2010 | Moon et al. | ........... | 514/243 |
| 7,932,384 B2 * | 4/2011 | Moon et al. | ........... | 544/184 |
| 8,049,008 B2 * | 11/2011 | Chung et al. | ........... | 544/184 |
| 8,071,764 B2 * | 12/2011 | Chung et al. | ........... | 544/184 |
| 8,080,657 B2 * | 12/2011 | Chung et al. | ........... | 544/184 |
| 8,101,751 B2 * | 1/2012 | Moon et al. | ........... | 544/184 |
| 8,106,049 B2 * | 1/2012 | Moon et al. | ........... | 514/243 |
| 8,138,337 B2 * | 3/2012 | Moon et al. | ........... | 544/184 |
| 8,318,738 B2 * | 11/2012 | Moon et al. | ........... | 514/243 |
| 8,729,262 B2 * | 5/2014 | Moon et al. | ........... | 544/184 |
| 2004/0072831 A1 | 4/2004 | Moon et al. | | |
| 2007/0021425 A1 | 1/2007 | Moon et al. | | |
| 2010/0267672 A1 | 10/2010 | Jung et al. | ........... | 514/81 |
| 2011/0257185 A1 | 10/2011 | Moon et al. | ........... | 514/243 |

FOREIGN PATENT DOCUMENTS

| | | |
|---|---|---|
| KR | 10 2010 0085102 A | 7/2010 |
| WO | WO 2009/005197 A1 | 1/2009 |
| WO | 2009/051399 A2 | 4/2009 |
| WO | WO 2009/148192 A1 | 12/2009 |
| WO | WO 2010/056311 A1 | 5/2010 |
| WO | WO 2010/120112 A2 | 10/2010 |
| WO | WO 2012/050393 A2 | 4/2012 |

OTHER PUBLICATIONS

He et al. Clinical Lung Cancer, vol. 7, No. 1, 54-60, 2005.*
Steward D.J, JNCI J Natl Cancer Inst (2014) 106(1): 1-11.*
Freshney et al.,Culture of Animal Cells, A Manual of Basic Technique, Alan R. Liss, Inc., 1983, New York, p. 4.*
Dermer et al., Bio/Technology, 1994, 12:320.*
J. Guillermo Paez, et al., "EGFR Mutations in Lung Cancer : Correlation with Clinical Reseponse to Gefitinib Therapy," Science, vol. 304, pp. 1497-1500 (Jun. 4, 2004).
S. Kobayashi, et al., "EGFR Mutation and Resistance of Non-Small-Cell Lung Cancer to Gefitinib," New England Journal of Medicine, vol. 352, No. 8, pp. 786-792 (Feb. 24, 2005).
W. Pao, et al., "Rational, biologically based treatment of EGFT-mutant non-small-cell lung cancer," Nature Reviews Cancer, vol. 10, pp. 760-774 (Nov. 2010).
A.G. Pallis, et al., "Biomarkers of clinical benefit for anti-epidermal growth factor receptor agents in patients with non-small-cell lung cancer," British Journal of Cancer, vol. 105, pp. 1-8 (2011).
Ma et al., "T790M and acquired resistance of EGFR TKI: a literature review of clinical reports," *Journal of Thoracic Disease* 3:10-18 (2010).
Zalcman et al., "Update on nonsmall cell lung cancer," *Eur Resp Rev* 19(117):173-185 (2010).

\* cited by examiner

*Primary Examiner* — Venkataraman Balasubramanian
(74) *Attorney, Agent, or Firm* — Seed IP Law Group PLLC

(57) ABSTRACT

Disclosed is a composition comprising a pyrazino-triazine derivative, an isomer thereof or a pharmaceutically acceptable salt thereof. It is very effective for preventing and treating NSCLC.

8 Claims, 11 Drawing Sheets

COMPOSITION FOR PREVENTING AND TREATING NON-SMALL CELL LUNG CANCER, CONTAINING PYRAZINO-TRIAZINE DERIVATIVES

BACKGROUND OF THE INVENTION

1. Field of the Invention

The present invention relates to a composition for the prevention and treatment of NSCLC (non-small cell lung cancer), comprising a pyrazino-triazine derivative.

2. Description of the Related Art

Primary lung cancer, which originates from the lung as implied by the term, is classified largely into small cell lung cancer and non-small cell lung cancer (NSCLC) according to histological type. Accounting for more than 80% of lung cancers, NSCLC is the highest cause of cancer-related death in the U.S.A, with a cure rate of less than 15% and an average survival period of 8~10 months. Once the cancer has progressed beyond the early stages, no surgical approaches are allowed, and the only resort is chemotherapy. However, NSCLC has poor sensitivity to anticancer agents because it is highly heterogeneous, consisting of different cell types.

For this reason, the doublet therapy of cytotoxic drugs is predominantly used to treat NSCLC. Among the cytotoxic drugs used for double therapy for NSCLC are carboplatin, paclitaxel, docetaxel and etoposide, with the preferential combination being paclitaxel and carboplatin. In addition, epidermal growth factor receptor tyrosine kinase inhibitor (EGFR TKI), a targeted therapeutic which inhibits epidermal growth factor (EGF), is commercially available under the brand names of Tarceva® and Irresa® as drugs for NSCLC.

Causing significant toxicity, the doublet therapy of those cytotoxic drugs is limitedly applied to patients who are physically weak, such as senile patients. In addition, this therapy can neither guarantee good anticancer efficiency nor a low recurrence rate for NSCLC patients in a very early or an advanced phase. Hence, there is a need for a newly established chemotherapy regimen targeting NSCLC centering on therapeutically excellent and non-toxic anticancer agents.

Targeted therapeutics, such as EGFR TKI, are applicable only to cancer patients who express specific target factors. For example, a clinical report has it that Tarceva® or Irresa® has high therapeutic effects particularly for some of the patients having a mutation on the epidermal growth factor receptor (active EGFR mutation (L858R, delE746_A750)), compared to patients having wild-type (WT) EGFR. This clinical response is attributable to the increased binding affinity of EGFR TKI for the mutated EGFR (Science Vol. 304, 4, Jun. 2004). However, in spite of the excellent anticancer activity of EGFR TKI on patients with the active mutation, many of the patients treated with EGFR TKI in 2005 have relapsed into chemoresistance to EGFR TKI, and an epigenetic analysis showed that the gatekeeper amino acid in EGFR TKI, threonine 790, is changed into methionine (T790M) in 50% of the relapsed patients (FIGS. 1 and 2). Crystallographic analysis shows that T790M mutation causes drug resistance by decreasing of binding affinity due to the steric hindrance at the binding position between Tarceva® and the methionine residue (NEJM Vol. 352, 8, Feb. 2005). In addition to the T790M mutation, other mutations including L747S, D761Y and T854A were also reported, but account for less than 10% of the relapses and thus are less important (Nature reviews cancer Vol. 10, 2010). There is insufficient data about which therapy is suitable for NSCLC patients having both the activation mutation and T790M (exon 20) (British Journal of Cancer 105(1), 1-8, 2011).

There is therefore a need for an agent that exhibits an excellent therapeutic effect on NSCLC in patients having an active mutation on EGFR as well as patients having WT EGFR and for patients relapsed into chemoresistance to EGFR TKI.

Meanwhile, WO12/050393, WO10/120112, WO09/05197 and WO09/148,192 disclose a number of compounds in the form of pyrazino-triazine derivatives which show anticancer activity. The therapeutic effects that the compounds mentioned above have on NSCLC is nowhere mentioned in the prior art documents. Among them, the compound derivatives represented by Chemical Formula 1 were surprisingly found by the present inventors to have therapeutic effects on NSCLC resistant to EGFR TKI.

SUMMARY OF THE INVENTION

It is an object of the present invention to provide a composition for the prevention and treatment of non-small cell lung cancer (NSCLC), comprising a pyrazino-triazine derivative.

It is another object of the present invention to provide a method for treating NSCLC, comprising administering a therapeutically effective amount of the composition to a subject in need thereof.

In accordance with an aspect thereof, the present invention provides a composition for the prevention or treatment of NSCLC, comprising at least one selected from the group consisting of a compound represented by the following Chemical Formula 1, an isomer thereof, and a pharmaceutically acceptable salt thereof:

[Chemical Formula 1]

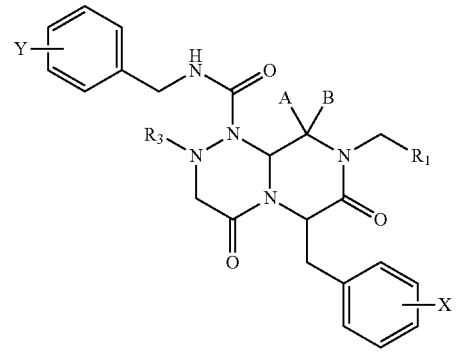

wherein, $R_1$ is substituted or unsubstituted C3-C10 aryl or substituted or unsubstituted C3-C10 heteroaryl with at least one nitrogen (N) atom; $R_3$ is hydrogen, C1~C6 alkyl, C2~C6 alkenyl, C2~C6 alkynyl, C3~C6 aryl, C3~C10 heteroaryl with at least one N atom, C3~C10 arylalkyl or C3~C10 heteroarylalkyl with at least one N atom; A is hydrogen or C1~C6 alkyl; B is hydrogen or C1~C6 alkyl; X is —O—PO$_3$H$_2$ or —OH; and Y is hydrogen, C3~C10 aryl, C3~C10 heteroaryl with at least one N atom or C1~C6 alkyl.

In one preferred embodiment of the present invention, the substituted C3~C10 aryl or the substituted C3~C10 heteroaryl with at least one N atom has at least one substituent selected from the group consisting of C1~C6 alkyl,

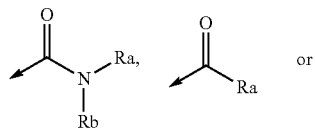

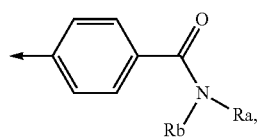

wherein Ra and Rb may be independently hydrogen, C1~C6 alkyl, pyridinyl, amino-substituted pyridinyl or amino-substituted pyridinyl, and may be condensed together to form a ring.

In another preferred embodiment of the present invention, $R_1$ is naphthyl, quinolinyl, indolyl, substituted naphthyl, substituted quinolinyl or substituted indolyl, wherein the substituted naphthyl, the substituted quinolinyl and the substituted indolyl have at least one substituent selected from C1~C6 alkyl,

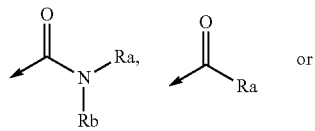

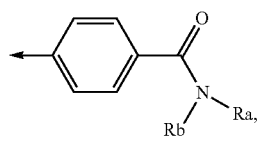

wherein Ra and Rb may be independently hydrogen, C1~C6 alkyl, pyridinyl or amino-substituted pyridinyl and may be condensed together to form a ring; $R_3$ is methyl or propenyl; either or both of A and B is hydrogen; X is —O—PO$_3$H$_2$ or —OH; and Y is hydrogen.

In a further embodiment of the present invention, the substituted naphthyl, the substituted quinolinyl or the substituted indolyl may have at least one substituent selected from

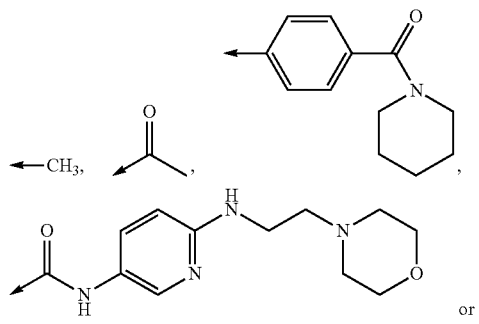

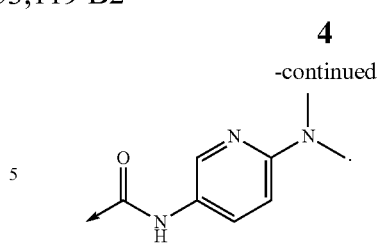

In an additional embodiment of the present invention, $R_1$ is

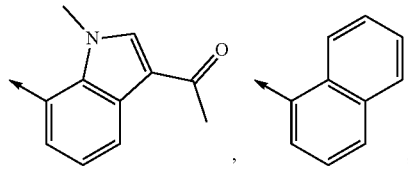

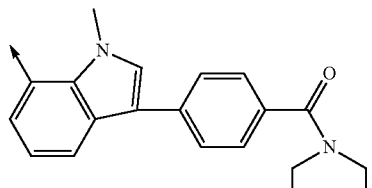

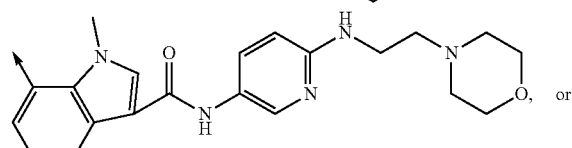

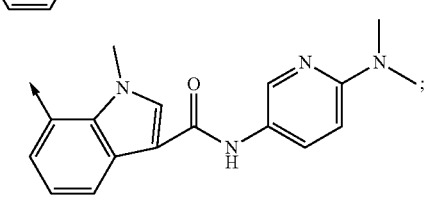

$R_3$ is

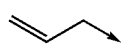

or methyl; either or both of A and B is hydrogen; X is —O—PO$_3$H$_2$ or —OH; and Y is hydrogen.

In a still further embodiment of the present invention, the compound of Chemical Formula 1 is selected from the group consisting of the compounds represented by the following Chemical Formulas 2 to 11:

| No. | Chemical Formula |
|---|---|
| 2 | 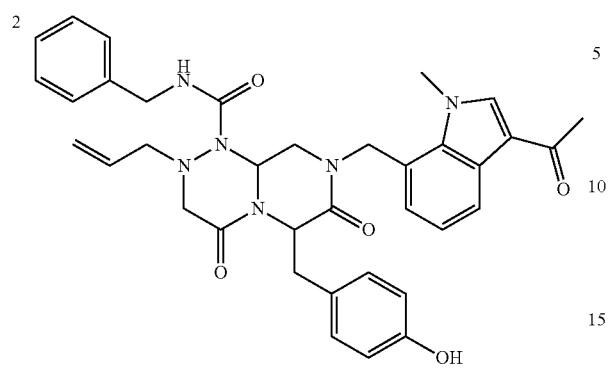 |
| 3 | 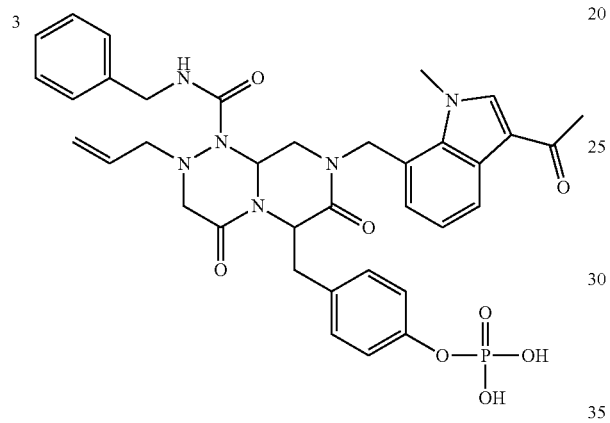 |
| 4 | 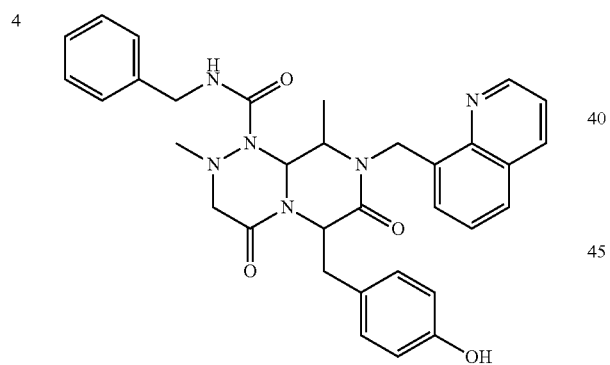 |
| 5 | 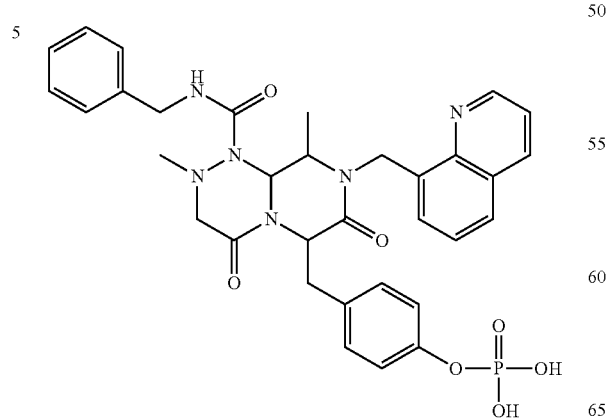 |
-continued
| No. | Chemical Formula |
|---|---|
| 6 | 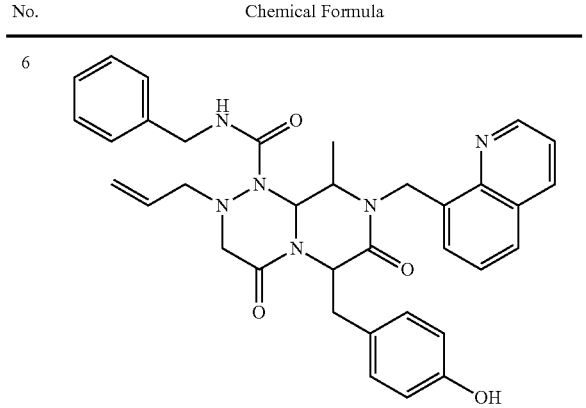 |
| 7 | 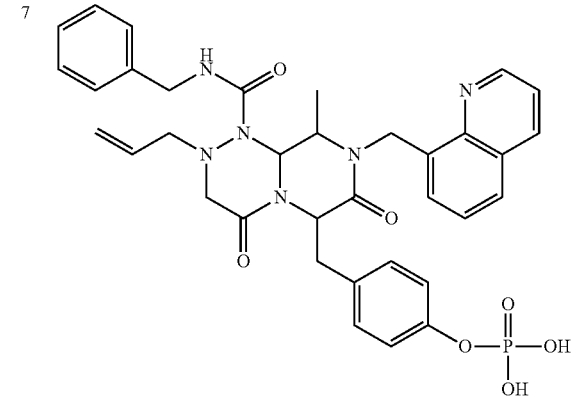 |
| 8 | 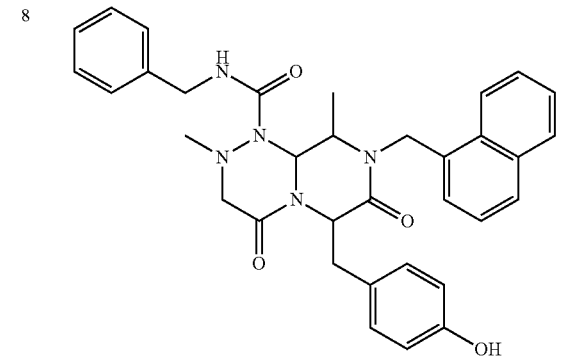 |
| 9 | 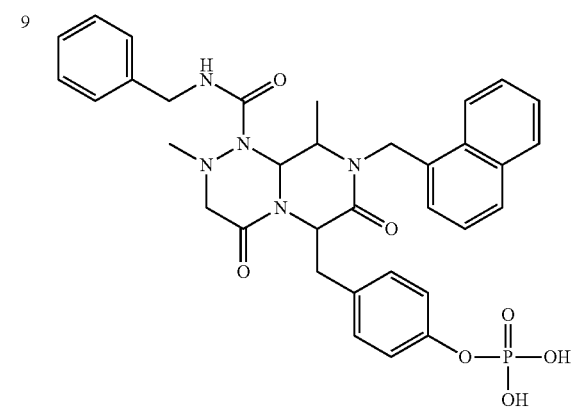 |

| No. | Chemical Formula |
|---|---|
| 10 | 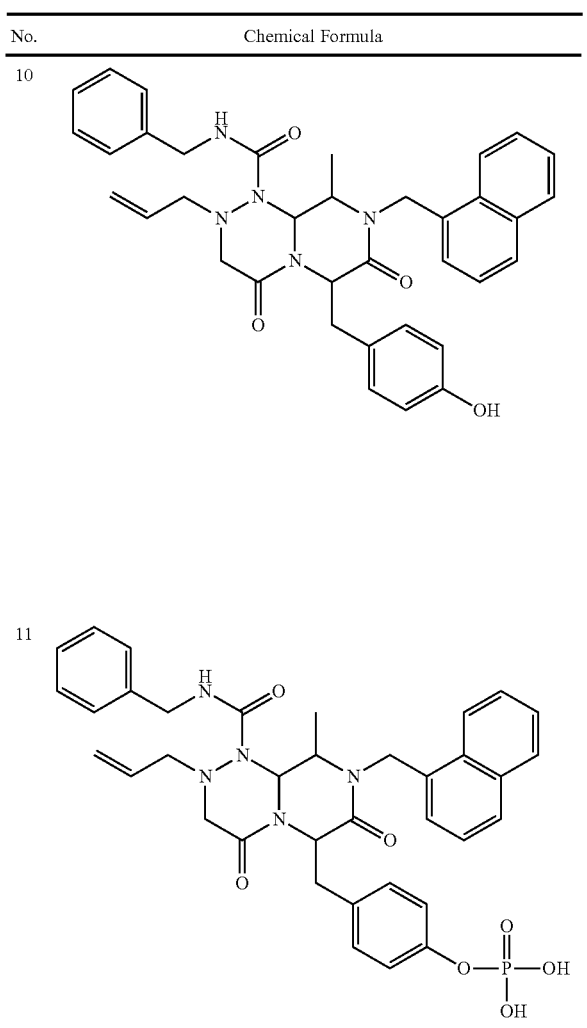 |
| 11 | |

| | [Chemical Formula 1-1] |
|---|---|
| | 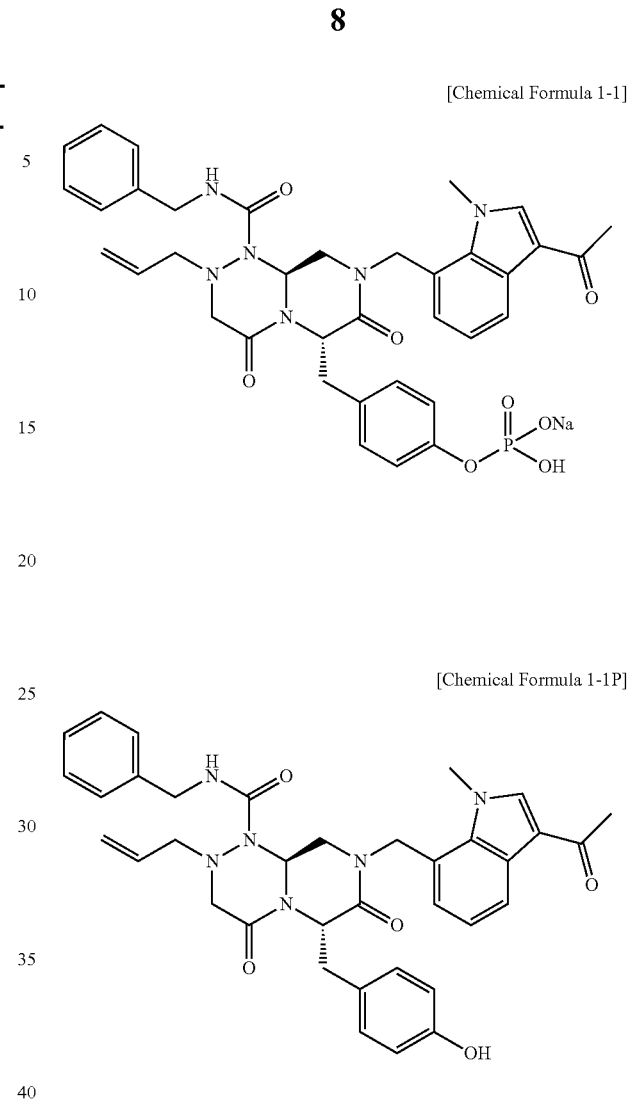 |
| | [Chemical Formula 1-1P] |

In still additional embodiment of the present invention, the compound of Chemical Formula 1 is selected from the group consisting of the compounds represented by the following Chemical Formulas 1-1 and 1-1P:

In yet still another embodiment of the present invention, the compound of Chemical Formula 1 is selected from the group consisting of the compounds represented by the following Chemical Formulas 1-2 to 1-7:

| No. | Chemical Formula |
|---|---|
| 1-2 | 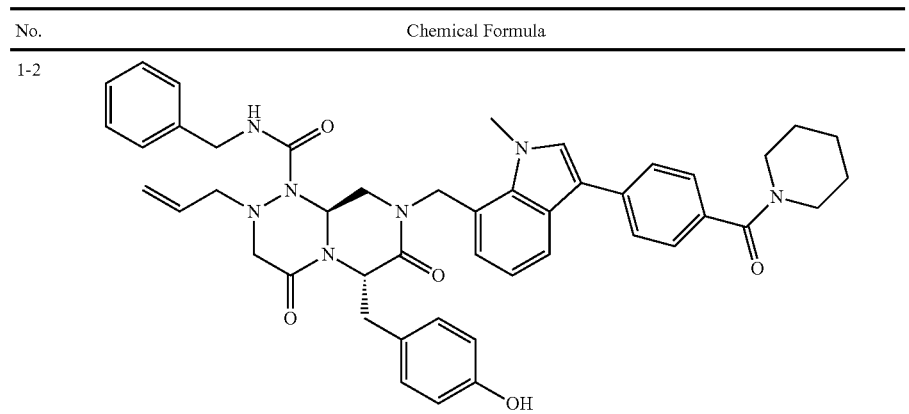 |

-continued
| No. | Chemical Formula |
|---|---|
| 1-3 | 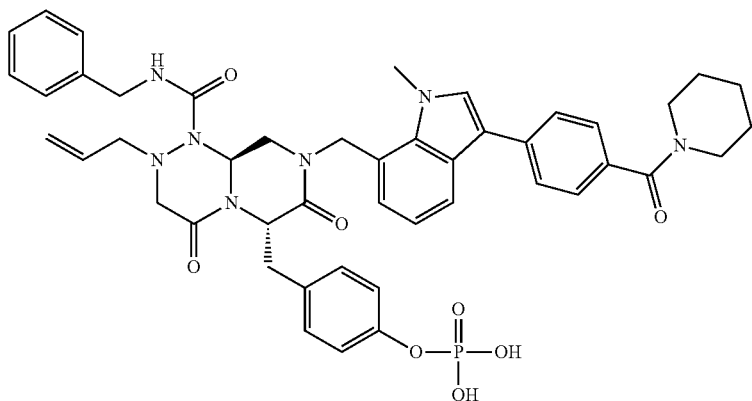 [SMILES: C=CCN1CC(=O)N2[C@@H](Cc3ccc(OP(=O)(O)O)cc3)C(=O)N(Cc3cccc4c(-c5ccc(C(=O)N6CCCCC6)cc5)cn(C)c34)C[C@@H]2N1C(=O)NCc1ccccc1] |
| 1-4 | 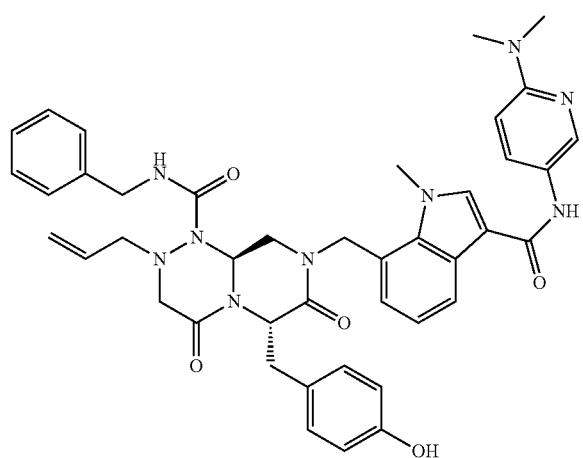 [SMILES: C=CCN1CC(=O)N2[C@@H](Cc3ccc(O)cc3)C(=O)N(Cc3cccc4c(C(=O)Nc5ccc(N(C)C)nc5)cn(C)c34)C[C@@H]2N1C(=O)NCc1ccccc1] |
| 1-5 | 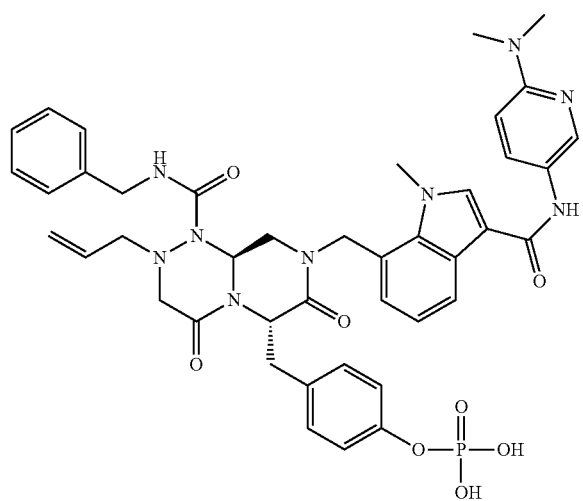 [SMILES: C=CCN1CC(=O)N2[C@@H](Cc3ccc(OP(=O)(O)O)cc3)C(=O)N(Cc3cccc4c(C(=O)Nc5ccc(N(C)C)nc5)cn(C)c34)C[C@@H]2N1C(=O)NCc1ccccc1] |

| No. | Chemical Formula |
|---|---|
| 1-6 | |
| 1-7 | |

In yet still a further embodiment of the present invention, the compound of Chemical Formula 1 is selected from the group consisting of the compounds represented by the following Chemical Formulas 2-1 to 2-8:

| No. | Chemical Formula |
|---|---|
| 2-1 | |
| 2-2 | |
| 2-3 | |

| No. | Chemical Formula |
|---|---|
| 2-4 | |
| 2-5 | |
| 2-6 | |
| 2-7 | |

| No. | Chemical Formula |
|---|---|
| 2-8 | |

According to one embodiment of the present invention, the NSCLC (non-small cell lung cancer) may have occurred in a patient having WT (wild-type) EGFR (epithelial growth factor receptor) or having an active mutation on EGFR.

According to another embodiment of the present invention, the NSCLC may be resistant to EGFR TKI and the cancer may be lung cancer.

According to a further embodiment of the present invention, the EGFR TKI-resistant cancer may have occurred in a patient having mutant EGFR.

According to still a further embodiment of the present invention, the mutant EGFR may have double mutations of L858R and T790M.

In accordance with another aspect thereof, the present invention provides a method for preventing or treating NSCLC (non-small cell lung cancer), comprising administering a therapeutically effective amount of a compound represented by the following Chemical Formula 1, an isomer thereof or a pharmaceutically acceptable salt thereof to a patient in need thereof:

[Chemical Formula 1]

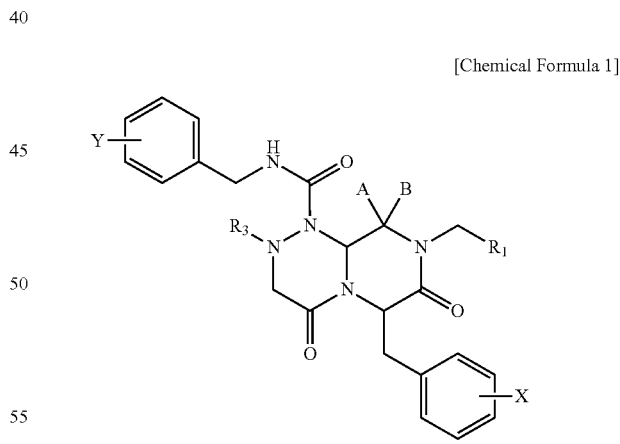

wherein,
$R_1$ is substituted or unsubstituted C3-C10 aryl or substituted or unsubstituted C3-C10 heteroaryl with at least one nitrogen (N) atom; $R_3$ is hydrogen, C1~C6 alkyl, C2~C6 alkenyl, C2~C6 alkynyl, C3~C6 aryl, C3~C10 heteroaryl with at least one N atom, C3~C10 arylalkyl or C3~C10 heteroarylalkyl with at least one N atom; A is hydrogen or C1~C6 alkyl; B is hydrogen or C1~C6 alkyl; X is —O—PO$_3$H$_2$ or —OH; and Y is hydrogen, C3~C10 aryl, C3~C10 heteroaryl with at least one N atom or C1~C6 alkyl.

The composition of the present invention is effective at treating NSCLC, and particularly at treating and preventing EGFR TKI-resistant NSCLC.

BRIEF DESCRIPTION OF THE DRAWINGS

The above and other objects, features and other advantages of the present invention will be more clearly understood from the following detailed description taken in conjunction with the accompanying drawings, in which.

DESCRIPTION OF THE PREFERRED EMBODIMENTS

Figure 1:
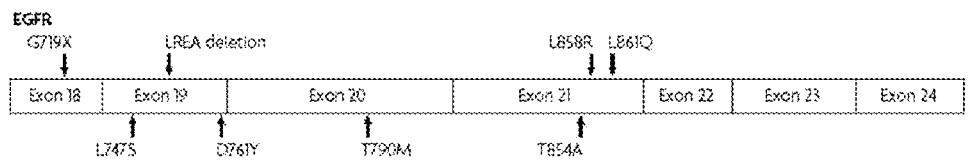
FIG. 1 is a schematic diagram of the structure of the EGFR gene and mutation loci.
Figure 2:
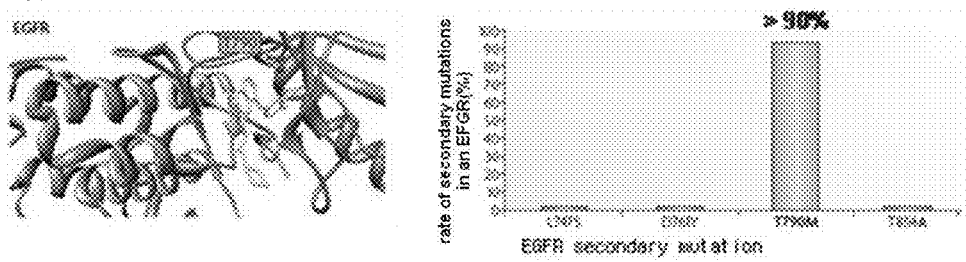
FIG. 2 shows a three dimensional structure of an EFGR in which a secondary mutation has occurred, and the rate of secondary mutations in an EFGR gene.
Figure 3:
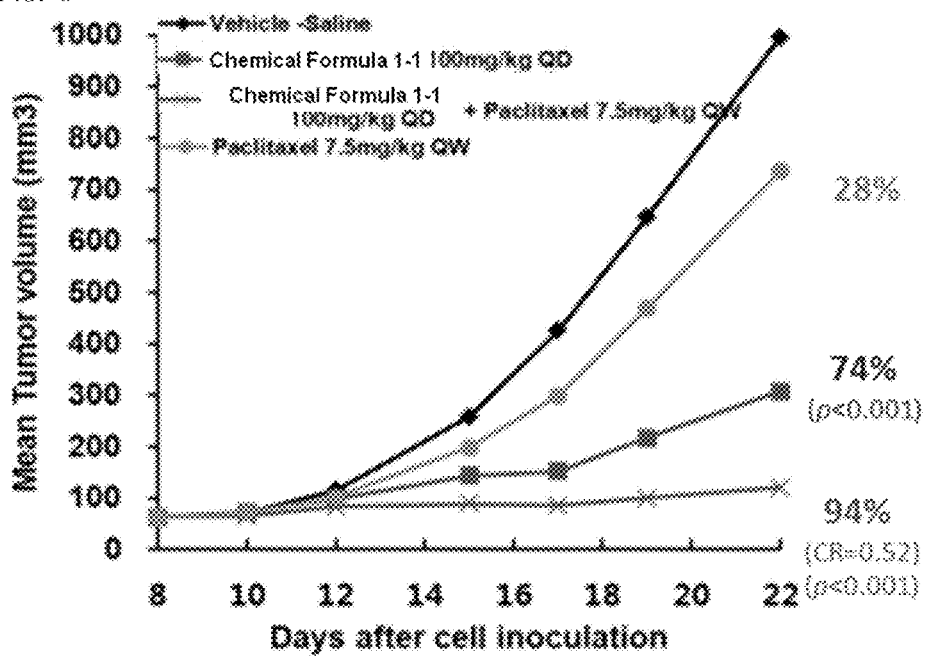
FIG. 3 is a graph in which mean tumor volumes (vertical axis) of the groups administered with the pyrazino-triazine derivative (Chemical Formula 1-1) at a low dose (100 mg/kg) are plotted against the days after cell inoculation (horizontal axis)
Figure 4:
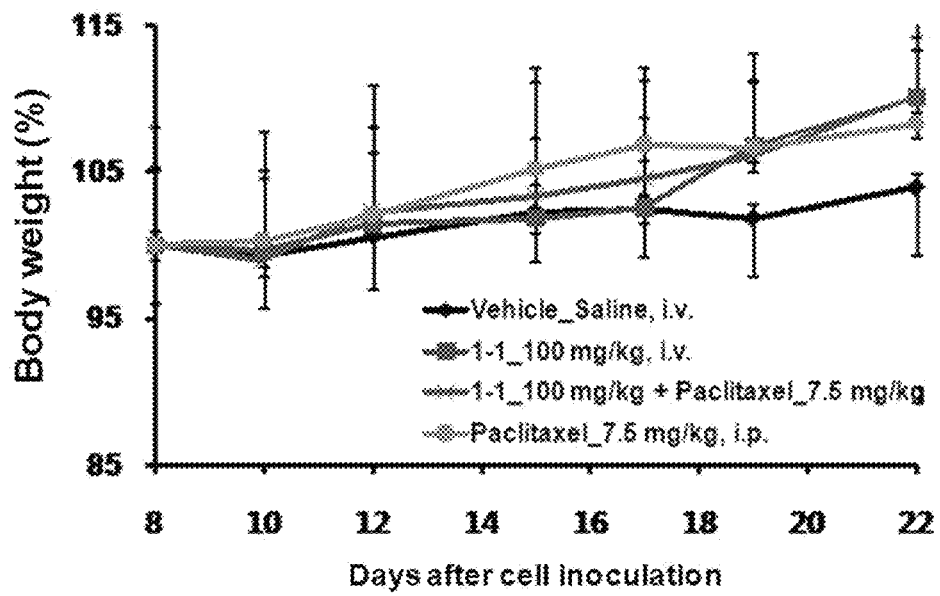
FIG. 4 is a graph in which body weights (vertical axis) of the groups administered with the pyrazino-triazine derivative (Chemical Formula 1-1) at a low dose (100 mg/kg) are plotted against the days after cell inoculation (horizontal axis), as compared to the body weight on D8.
Figure 5:
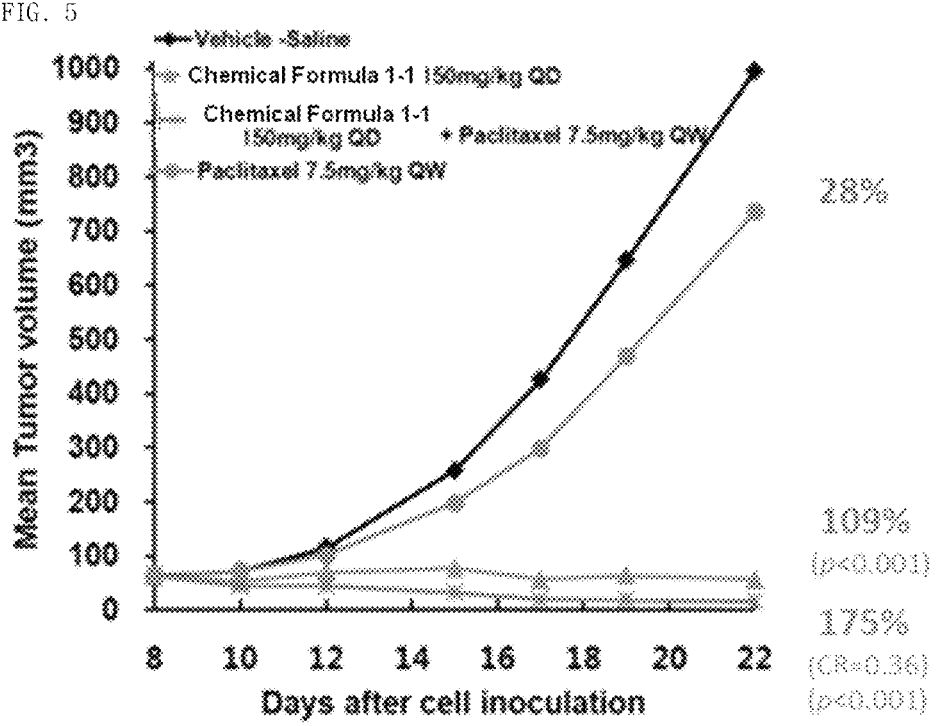
FIG. 5 is a graph in which mean tumor volumes (vertical axis) of the groups administered with the pyrazino-triazine derivative (Chemical Formula 1-1) at a high dose (150 mg/kg) are plotted against the days after cell inoculation (horizontal axis)
Figure 6:
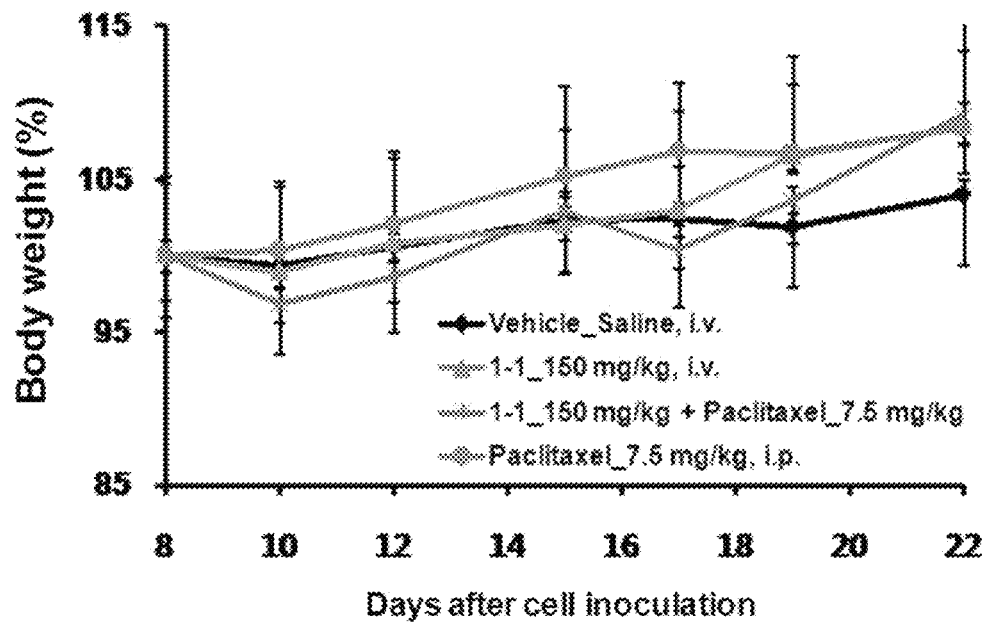
FIG. 6 is a graph in which body weights (vertical axis) of the groups administered with the pyrazino-triazine derivative (Chemical Formula 1-1) at a high dose (150 mg/kg) are plotted against the days after cell inoculation (horizontal axis), as compared to the body weight on D8.

The present invention addresses a composition for the prevention or treatment of NSCLC (non-small cell lung cancer), comprising a pyrazino-triazine derivative as an active ingredient.

The present inventors found and proved that the pyrazino-triazine derivative of the present invention is effective in the therapy and prophylaxis of cancer showing chemoresistance, which culminated in the present invention.

As used herein, the term "pyrazino-triazine derivative" refers to a compound represented by the following Chemical Formula 1.

In detail, the pyrazino-triazine derivative of the present invention may be selected from the group consisting of a compound represented by the following Chemical Formula 1, an isomer thereof and a pharmaceutically acceptable salt thereof, but is not limited thereto:

[Chemical Formula 1]

wherein, $R_1$ is substituted or unsubstituted C3-C10 aryl or substituted or unsubstituted C3-C10 heteroaryl with at least one nitrogen (N) atom. The substituted C3~C10 aryl or the substituted C3~C10 heteroaryl with at least one N atom may have at least one substituent selected from the group consisting of C1~C6 alkyl, wherein Ra and Rb may be independently hydrogen, C1~C6 alkyl, pyridinyl, amino-substituted pyridinyl or amino-substituted pyridinyl, and may be condensed together to form a ring.

Preferably, $R_1$ is naphthyl, quinolinyl, indolyl, substituted naphthyl, substituted quinolinyl or substituted indolyl, wherein the substituted naphthyl, the substituted quinolinyl and the substituted indolyl have at least one substituent selected from C1~C6 alkyl,

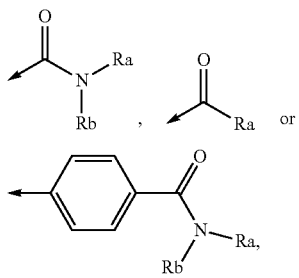

wherein Ra and Rb may be independently hydrogen, C1~C6 alkyl, pyridinyl or amino-substituted pyridinyl and may be condensed together to form a ring. In addition, the substituted naphthyl, the substituted quinolinyl or the substituted indolyl may have at least one substituent selected from

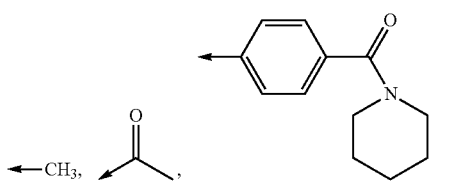

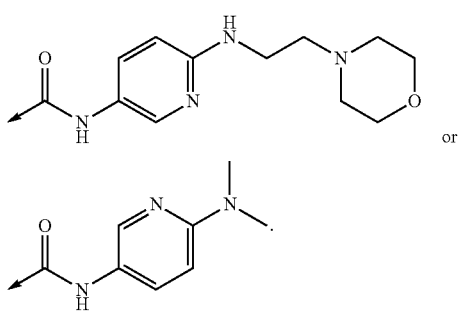

In detail, $R_1$ is

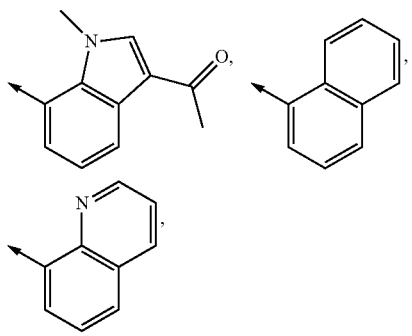

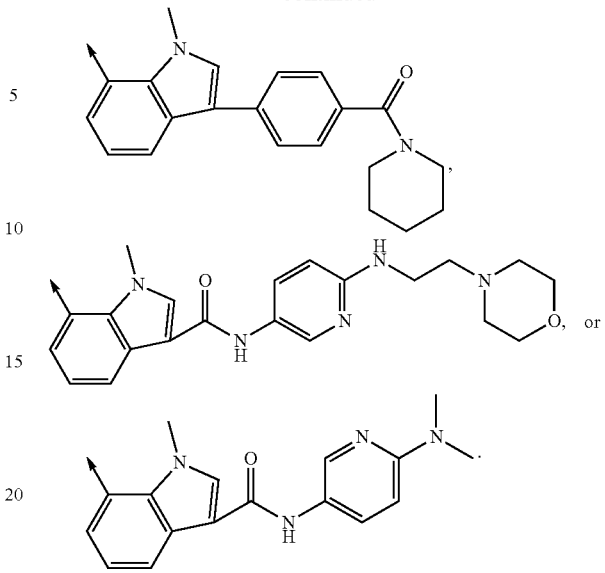

In Chemical Formula 1, $R_3$ is hydrogen, C1~C6 alkyl, C2~C6 alkenyl, C2~C6 alkynyl, C3~C6 aryl, C3~C10 heteroaryl with at least one N atom, C3~C10 arylalkyl or C3~C10 heteroarylalkyl with at least one N atom, and preferably is methyl or propenyl

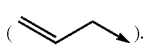

In Chemical Formula 1, A is hydrogen or C1~C6 alkyl and B is hydrogen or C1~C6 alkyl. Preferably, either or both of A and B is hydrogen.

In Chemical Formula 1, X is —O—PO$_3$H$_2$ or —OH.

In Chemical Formula 1, Y is hydrogen, C3~C10 aryl, C3-C10 heteroaryl with at least one N atom or C1~C6 alkyl, with preference for hydrogen.

In greater detail, the pyrazino-triazine derivative of the present invention may be selected the group consisting of the compound represented by one of the following Chemical Formulas 2 to 11, an isomer thereof, a pharmaceutically acceptable salt thereof, and a combination thereof:

| No. | Chemical Formula |
|---|---|
| 2 | 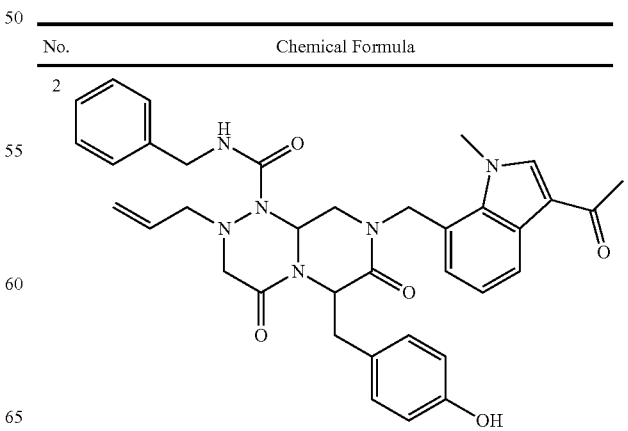 |

19
-continued
| No. | Chemical Formula |
|---|---|
| 3 | |
| 4 | |
| 5 | |
| 6 | |
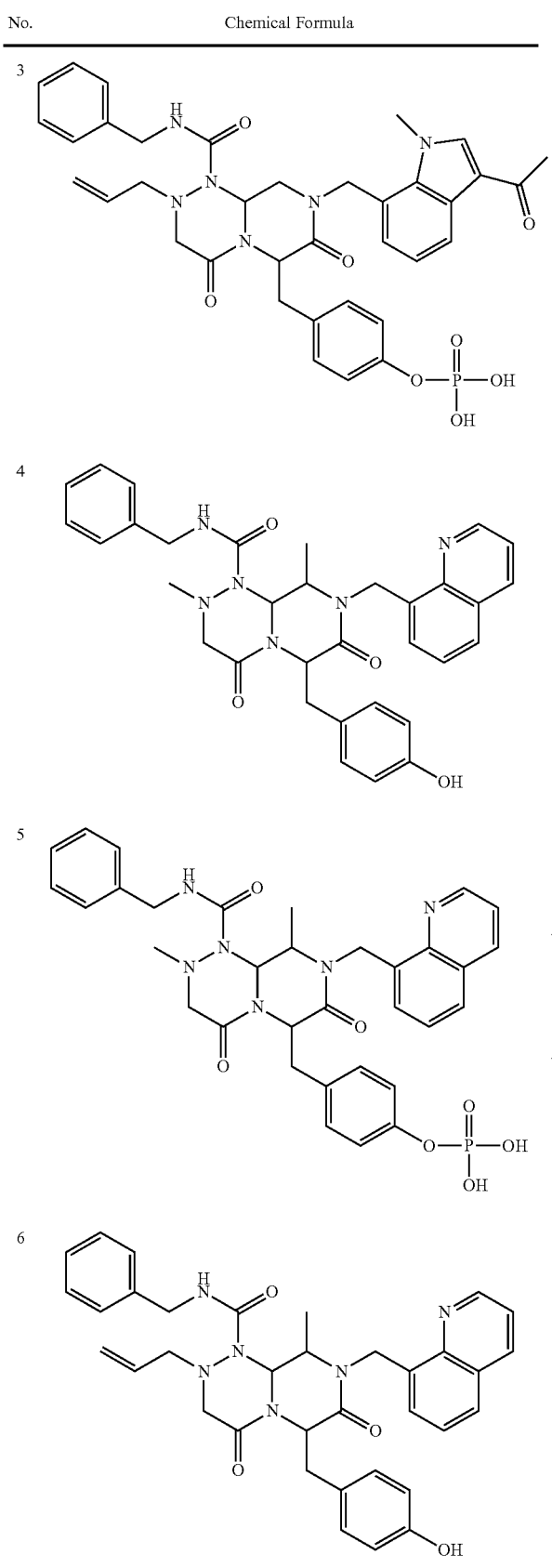
20
-continued
| No. | Chemical Formula |
|---|---|
| 7 | |
| 8 | |
| 9 | |
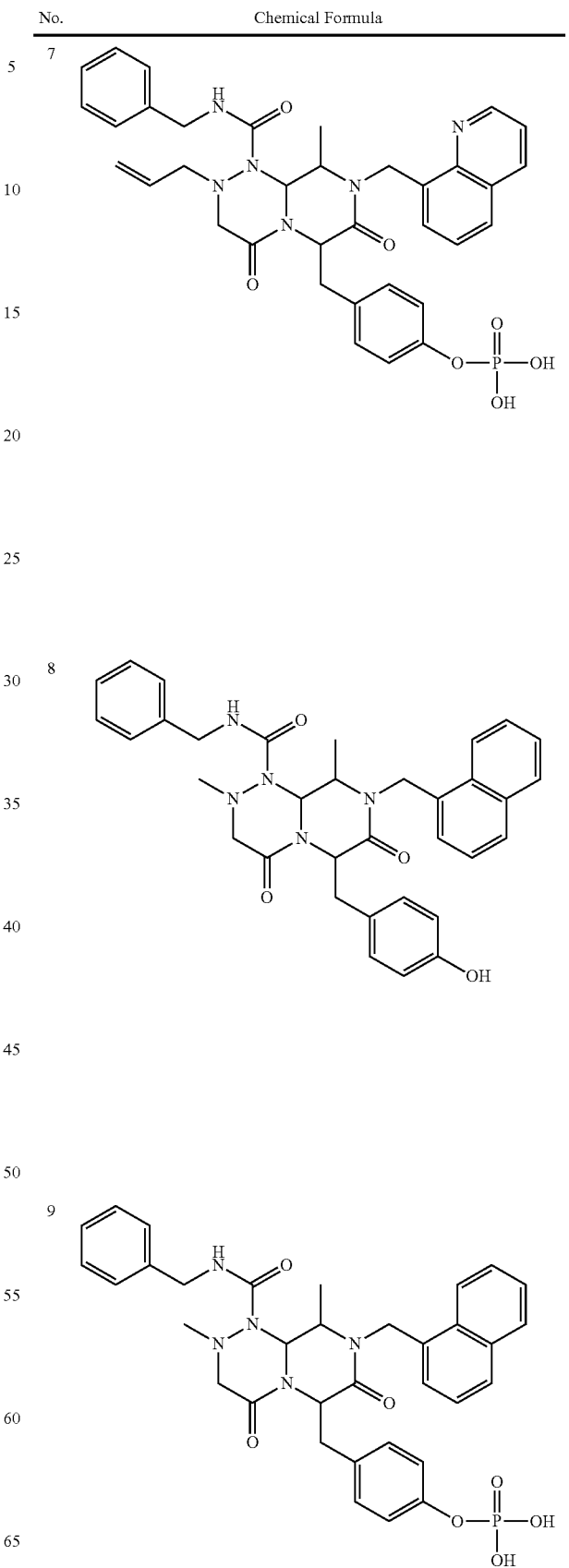

| No. | Chemical Formula |
|---|---|
| 10 | 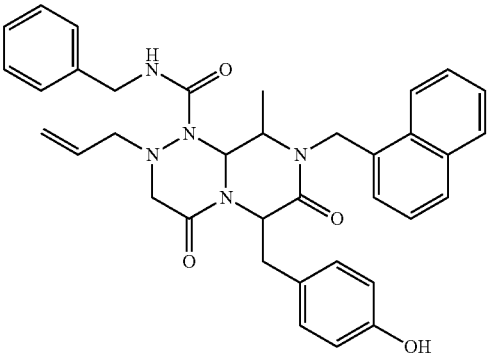 [SMILES: C=CCN1CC(=O)N2C(Cc3ccc(O)cc3)C(=O)N(Cc3cccc4ccccc34)C(C)C2N1C(=O)NCc1ccccc1] |
| 11 | 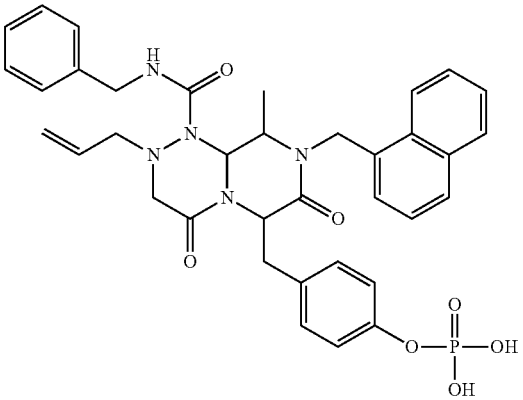 [SMILES: C=CCN1CC(=O)N2C(Cc3ccc(OP(=O)(O)O)cc3)C(=O)N(Cc3cccc4ccccc34)C(C)C2N1C(=O)NCc1ccccc1] |

The pyrazino-triazine derivative of the present invention may be the compound represented by the following Chemical Formula 1-1 or 1-1P:

[Chemical Formula 1-1]

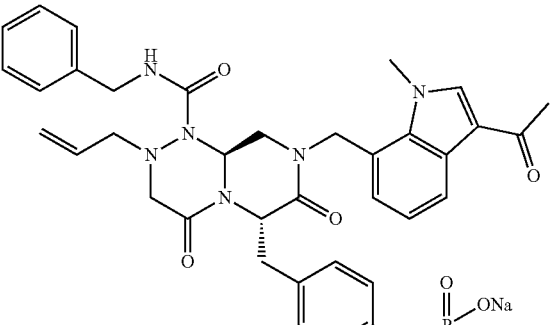

[Chemical Formula 1-1P]

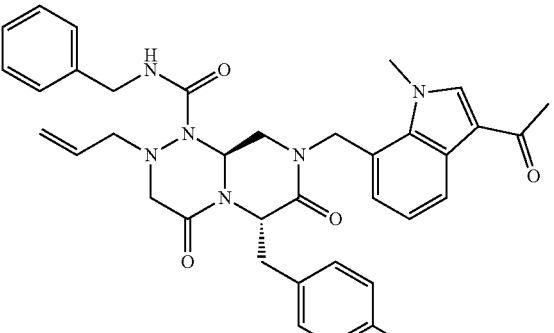

Also, the pyrazino-triazine derivative of the present invention may be a compound selected from the group consisting of the compounds represented by the following Chemical Formulas 1-2 to 1-7, and pharmaceutically acceptable salts thereof:

| No. | Chemical Formula |
|---|---|
| 1-2 | 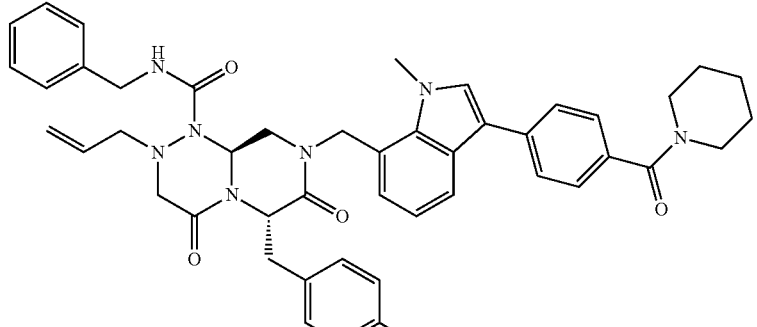 |

| No. | Chemical Formula |
|---|---|
| 1-3 | 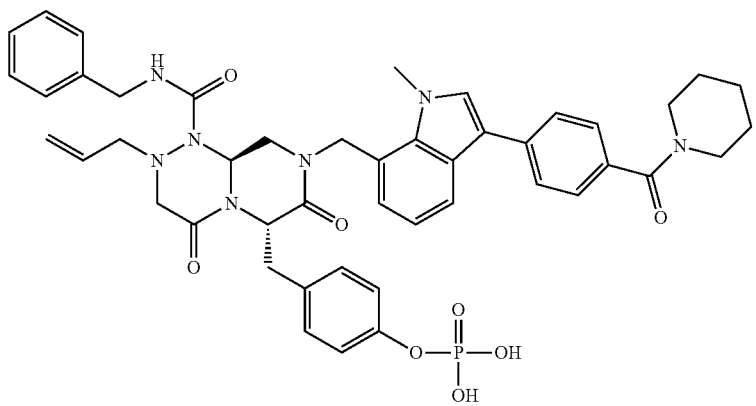 [SMILES: C=CCN1CC(=O)N2[C@@H](Cc3ccc(OP(=O)(O)O)cc3)C(=O)N(Cc3cccc4c(-c5ccc(C(=O)N6CCCCC6)cc5)cn(C)c34)C[C@@H]2N1C(=O)NCc1ccccc1] |
| 1-4 | 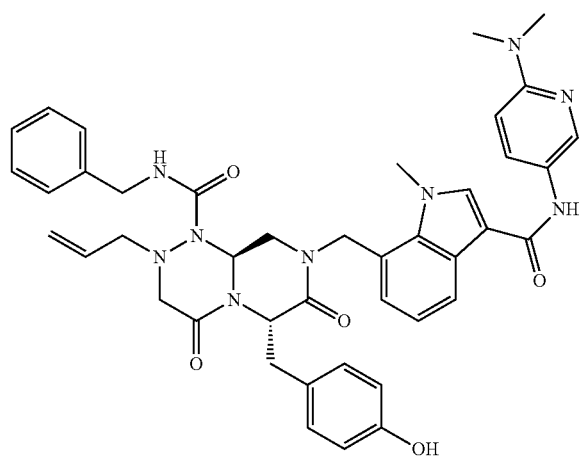 [SMILES: C=CCN1CC(=O)N2[C@@H](Cc3ccc(O)cc3)C(=O)N(Cc3cccc4c(C(=O)Nc5ccc(N(C)C)nc5)cn(C)c34)C[C@@H]2N1C(=O)NCc1ccccc1] |
| 1-5 | 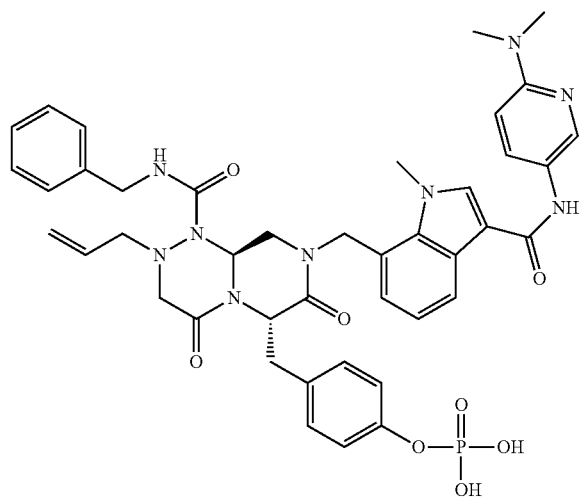 [SMILES: C=CCN1CC(=O)N2[C@@H](Cc3ccc(OP(=O)(O)O)cc3)C(=O)N(Cc3cccc4c(C(=O)Nc5ccc(N(C)C)nc5)cn(C)c34)C[C@@H]2N1C(=O)NCc1ccccc1] |

-continued
| No. | Chemical Formula |
|---|---|
| 1-6 | 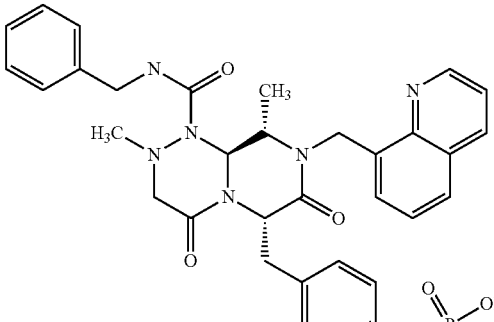 |
| 1-7 | 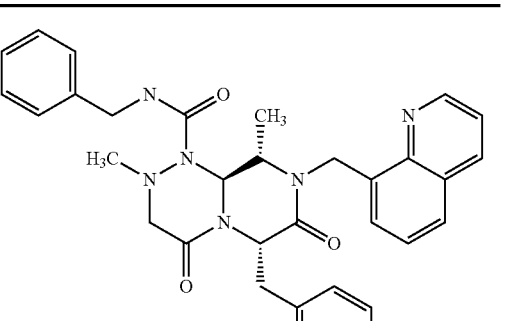 |
Also, the pyrazino-triazine derivative of the present invention may be a compound selected from the group consisting of the compounds represented by the following Chemical Formulas 2-1 to 2-8, and pharmaceutically acceptable salts thereof:
| No. | Chemical Formula |
|---|---|
| 2-1 | |
| 2-2 | |
| 2-3 | |
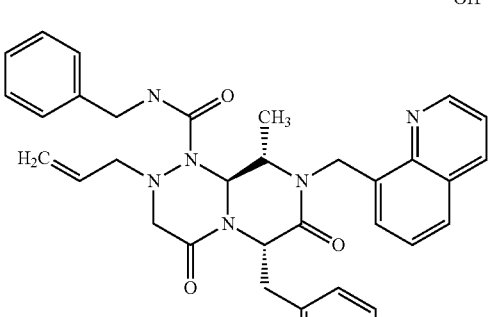

| No. | Chemical Formula |
|---|---|
| 2-4 | |
| 2-5 | |
| 2-6 | |
| No. | Chemical Formula |
|---|---|
| 2-7 | |
| 2-8 | |
The pyrazino-triazine derivative of the present invention may be prepared according to the following Reaction Scheme 1.
[Reaction Scheme 1]
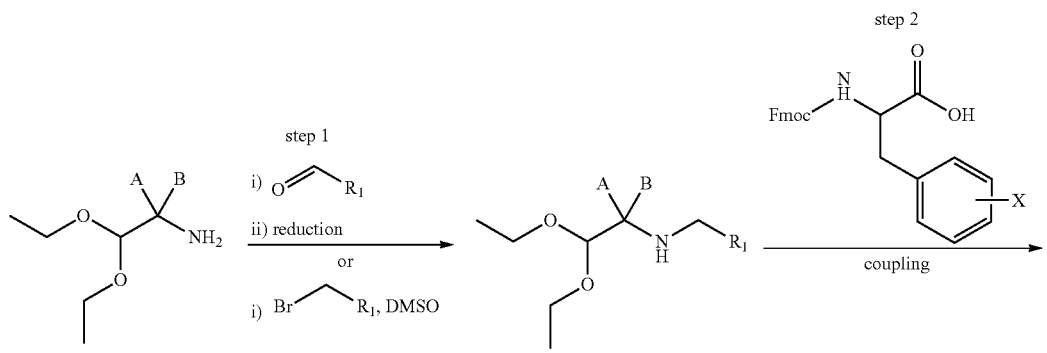

-continued
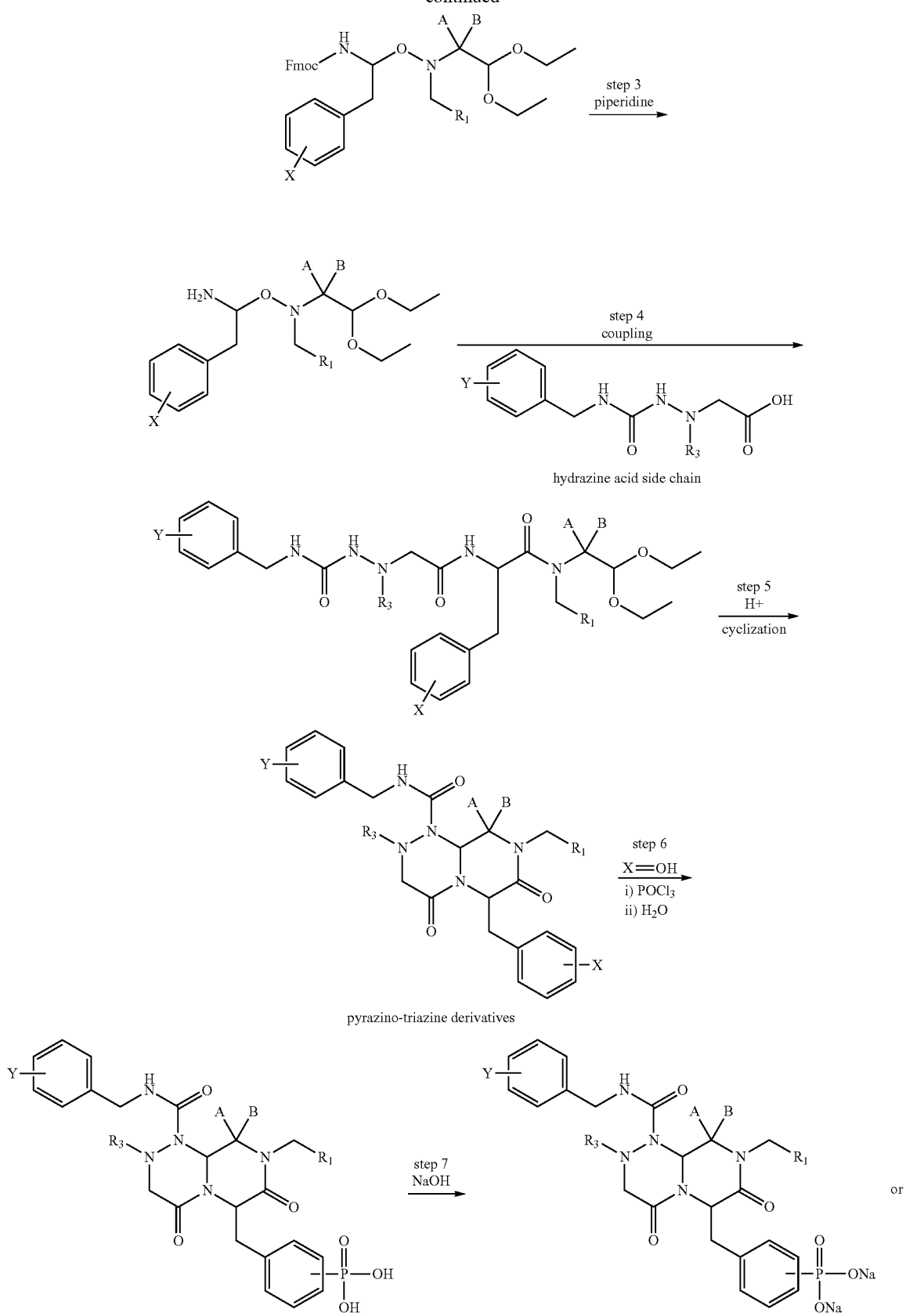
hydrazine acid side chain
pyrazino-triazine derivatives
or

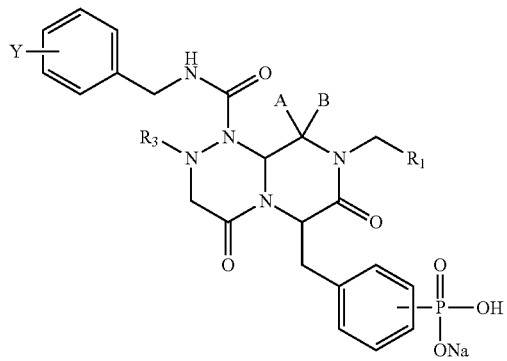

wherein A, B, $R_1$, $R_3$, X, and Y are each as defined above.

As seen in Reaction Scheme 1, the pyrazino-triazine derivative of the present invention can be prepared in the following sequential steps:

Step 1: substituted aminoacetal is reacted with aldehyde or alkyl halogen;

Step 2: the resulting substituted aminoacetal of step 1 is coupled with an amino acid to form a peptide;

Step 3: the peptide of step 2 is deprotected with a salt;

Step 4: the deprotected peptide of step 3 is coupled with a hydrazine acid side chain;

Step 5: the resulting peptide of step 4 is cyclized under an acidic condition to form a pyrazino-triazine derivative;

Step 6: a phosphate group is introduced into the pyrazino-triazine derivative of step 5 when X is hydroxy;

Step 7: the phosphorylate group introduced in step 6 is converted into a mono- or disodium salt.

As used herein, the term "pharmaceutically acceptable salt" refers to a salt used typically in the pharmaceutical field. Examples of the pharmaceutically acceptable salt include sodium salts, chlorides, magnesium salts, calcium salts and potassium salts, but are not limited thereto. Preferred is a sodium salt or a chloride.

The composition of the present invention can be useful for treating or preventing NSCLC (non-small cell lung cancer).

The NSCLC may have occurred in a patient having WT (wild-type) EGFR or having an active mutation on EGFR.

Also, the NSCLC may be cancer occurring in a patient having an active mutation on EGFR. The active mutation may be selected from among L858R, E746 deletion, A750 deletion and a combination thereof. The cancer occurring in a patient having such an active mutation on EGFR may be an EGFR TKI-sensitive cancer. In the present invention, the term "EGFR TKI" is an abbreviation for Epidermal Growth Factor Receptor Tyrosine Kinase Inhibitor, which inhibits the activity of EGF (Epidermal Growth Factor), but encompasses all agents having such activity. In the present invention, the term "EGFR TKI-sensitive cancer" means cancer on which EGFR TKI exhibits particularly high therapeutic effects.

In addition, the NSCLC may be EGFR TKI resistant cancer. As used herein, the term "EGFR TKI resistant cancer" is intended to encompass cancer showing chemoresistance to EGFR TKI. It may be cancer caused by a mutation in the EGFR. The mutation may further has the mutation selected from T790M, L747S, D761Y, T854A and a combination thereof, in addition to the above active mutation. Preferred is a double mutation of L858R and T790M.

The EGFR TKI-resistant cancer also encompasses cancer that has relapsed after the administration of EGFR TKI, and cancer occurring in individuals having a mutant EGFR resistant to EGFR TKI.

Further, the NSCLC treated by the present invention may have wild-type KRAS or mutant KRAS.

Accordingly, the composition of the present invention exhibits excellent therapeutic effects on NSCLC patients whether they have wild-type EGFR or an active mutation on EGFR or show resistance to EGFR TKI.

The composition of the present invention may further comprise pharmaceutically acceptable additives such as diluents, binders, disintegrants, lubricants, pH-adjusting agents, antioxidants and solubilizers, within the range where effects of the present invention are not impaired.

In addition, the composition of the present invention may be formulated into a delayed-release form, together with an enteric polymer, a water-insoluble polymer, a hydrophobic compound and a hydrophilic polymer. The enteric polymer refers to a polymer which is insoluble or stable under the acidic conditions of less than pH 5, and is dissolved or degraded under the specific pH conditions of pH 5 or higher.

In addition, the formulation of the present invention may optionally contain pharmaceutically acceptable additives such as various additives selected from a colorant and a fragrance.

The range of the additive that can be used in the present invention is not limited to the above-mentioned additives, and the additive may be used in a conventional dose which can be suitably selected by those skilled in the art.

Using a conventional method, the pharmaceutical composition of the present invention may be formulated into oral dosage forms such as powders, granules, tablets, capsules, suspensions, emulsions, syrups and aerosols, external applications, suppositories, or sterile injections.

In accordance with still another aspect thereof, the present invention provides a method for preventing or treating NSCLC, comprising administering to a subject including a mammal the composition comprising the compound of the present invention.

The term "administration," as used herein, refers to the introduction of the composition for the prevention and treatment of NSCLC of the present invention into a subject in an appropriate manner. So long as it leads the composition of the present invention to a target tissue, any administration route may be taken. Examples of the route through which the composition for the prevention and treatment of NSCLC in accordance with the present invention may be administered include the oral, intraperitoneal, intravenous, intramuscular, subcutaneous, intradermal, intranasal, intrapulmonary, intrarectal, intravesicular, and intradural routes, but are not limited thereto.

The composition for the prevention or treatment of NSCLC in accordance with the present invention may be administered once a day or twice a day at regular intervals.

The dosage levels of the compounds of the present invention vary depending on various factors including the patient's weight, age, sex, health state, and diet, the time of administration, the route of administration, the excretion rate, the severity of disease, etc. The active ingredient may be administered at a dose of from 0.1 to 300 mg/kg/day and preferably at a dose of from 0.5 to 200 mg/kg/day, but the amount may vary depending on the patient's age and gender, the severity of the disease, etc.

In accordance with a further aspect thereof, the present invention addresses a method for treating NSCLC, comprising administering a therapeutically effective amount of the compound of the present invention to a patient in need thereof.

In one preferred embodiment of the present invention, the treating method of the present invention may comprise administering the pharmaceutical composition comprising the compound of the present invention, in combination with one or more anticancer drugs.

One of the known anticancer agents may be paclitaxel. The pharmaceutically effective amount of the known anticancer agent is also known in the art and the final dosage regimen will be determined by the attending physician, in light of various factors including the co-administration together with the composition of the present invention. When co-administered together with a conventional anticancer agent, the composition of the present invention can confer a therapeutically synergistic effect in addition to reducing the side effects of the anticancer agent. The conventional anticancer agent may be administered as a complex formulation or simultaneously with the composition of the present invention, or separately at time intervals different from the administration of the composition of the present invention.

A better understanding of the present invention may be obtained through the following examples which are set forth to illustrate, but are not to be construed as limiting the present invention.

For the preparation of the compounds used in the present invention, reference may be made to Reaction Scheme 1, or WO12/050,393, WO10/120,112, WO09/051,397 or WO09/148,192.

EXPERIMENTAL EXAMPLE 1

Therapeutic Effect of Chemical Formula 1-1 on NSCLC of EGFR TKI Resistant Cells (NCI-H1975)

1) Purpose

This experiment aims to evaluate the in vivo anticancer activity of the pyrazino-triazine derivatives (Chemical Formula 1-1) of the present invention in animals transplanted with NCI-H1975 cells, a kind of NSCLC cell resistant to EGFR-targeted agents.

2) Methods

NCI-H1975 (ATCC, CRL-5908), derived from NSCLC patients, is an NSCLC cell line having a double mutation of EGFR L858R and T790M, which is highly resistant to EGFR TKI (Tarceva®, Iressa®). These cells were used to evaluate in vivo anticancer activity of the compounds of the present invention. In this context, NCI-H1975 cells were cultured on a mass scale, and subcutaneously transplanted at a density of $5 \times 10^6$ cells in 0.2 mL of HBSS per head into the right axillar region of mice (Balb/c nude mice). Three to five days after the transplantation, tumor masses were observed. From Day 8 (D8) to Day 22 (D22) after the transplantation, six groups of the NCI-H1975-transplanted mice were administered with compound of Chemical Formula 1-1 and/or paclitaxel as summarized in Table 1, below.

TABLE 1

| Group | Administered Substance and Amount thereof |
|---|---|
| 1 | Vehicle Saline |
| 2 | 1-1__100 mg/kg |
| 3 | 1-1__150 mg/kg |
| 4 | 1-1__100 mg/kg + Paclitaxel__7.5 mg/kg |
| 5 | 1-1__150 mg/kg + Paclitaxel__7.5 mg/kg |
| 6 | Paclitaxel__7.5 mg/kg |

As the control, only a vehicle was intravenously injected once a day to reach a total of ten injections over a two week period (five times per week, D8~12, 15~19) (Group 1).

The compound of Chemical Formula 1-1 was dissolved in saline and intravenously injected at a dose of 100 and 150 mg/kg once a day to reach a total of ten injections over a two week period (five times per week, D8~12, 15~19) (Groups 2 and 3, respectively).

Paclitaxel was intraperitoneally injected at a dose of 7.5 mg/kg once a day to reach a total of two injections over two weeks (once a week, D8 and D5) (Group 6).

The compound of Chemical Formula 1-1 was injected at a dose of 100 mg/kg and 150 mg/kg to the mice administered with paclitaxel at a dose of 7.5 mg/kg in the same manner as described above (Groups 4 and 5).

3) Results i. Changes in Body Weight and Tumor Size and Evaluation of Tumor Growth Inhibition (TGI)

Body weights and tumor sizes of the mice were measured two or three times per week during the experiment.

Measurements of body weights and tumor sizes were randomized for n=7 per group using in-house randomization software. The tumor size was calculated from measurements of the longest axis (length, m) and the shortest axis (width, m) according to the following formula:

$$\text{Tumor size (mm}^3\text{): Width (mm)} \times \text{Width (mm)} \times \text{Length (mm)}/2$$

On D8, the mice had a mean tumor size of 63 mm$^3$ (range=42~103 mm$^3$), with a mean body weight of 18.6 g.

On D22, as can be seen in Table 3, the vehicle control had a final tumor size of 995±131 mm$^3$ while the tumor in the Chemical Formula 1-1 (P1)-administered group was significantly reduced.

Therefore, the data indicate that the compound of the present invention exhibits excellent anticancer activity in EGFR TKI-resistant NSCLC cell lines having a double mutation of L858R and T790M.

The anticancer activity depending on the administration was evaluated by tumor growth inhibition, (TGI, %) calculated according to the following formulas.

When the tumor size of the drug-administered group is larger than the initial tumor size:

$$\% \text{ TGI}=100*(1-(\text{tumor volume}_{Day\ X}-\text{tumor volume}_{Initial\ for\ treated\ group})/(\text{tumor volume}_{Day\ X}-\text{tumor volume}_{Initial\ for\ Vehicle\ group}))$$

When the tumor size of the drug-administered group is smaller than the initial tumor size:

$$\% \text{ TGI}=100+100*(1-(\text{Treated group tumor volume}_{Day\ X}/\text{Treated group tumor volume}_{initial}))$$

The administration of Chemical Formula 1-1 elicited TGI 74% upon a dose of 100 mg/kg and TGI 109% upon a dose of 150 mg/kg, showing anticancer activity in a dose-dependent manner.

These results are far greater than those obtained by paclitaxel, which were measured to be TGI 28% at a dose of 7.5 mg/kg.

In addition, in the groups administered with a combination of Chemical Formula 1-1 (100, 150 mg/kg) and paclitaxel (7.5 mg/kg), TGI was measured to be 94% and 175%, respectively, demonstrating a synergistic effect achieved by their combined administration.

Results are summarized in Tables 2 and 3 and are depicted in FIGS. 3 to 6.

ii. Mortality and Maximum Body weight Loss (MBL)

Herein, mortality indicated deaths resulting from drug administration. During and after this experiment, no case of death was observed in any group.

Herein, maximum body weight loss (MBL) means the largest loss of body weight caused by drug administration and is an important factor for determining maximum tolerable dose (MTD). The change of body weight was expressed as percentage of the body weight just before drug administration (D1). As a rule, the dose at which 10% or more of the body weight was lost was determined as the MTD.

Measurements are summarized in Table 2, below.

TABLE 2

| Group | Mortality | Tumor size @D 22 (Mean ± S.E. mm3) | TGI(%) D22 | MBL (%) |
|---|---|---|---|---|
| 1 | 0/7 | 995 ± 131 | — | — |
| 2 | 0/7 | 307 ± 97 | 74 | — |
| 3 | 0/7 | 57 ± 22 | 109 | — |
| 4 | 0/7 | 120 ± 32 | 94 | — |
| 5 | 0/7 | 16 ± 5 | 175 | 3 (D16) |
| 6 | 0/7 | 736 ± 79 | 28 | — |

EXPERIMENTAL EXAMPLE 2

Therapeutic Effect of Chemical Formula 1-1 on NSCLC of EGFR TKI Resistant Cell (NCI-H460)

1) Purpose

This experiment aims to evaluate the in vivo anticancer activity of the pyrazino-triazine derivatives (Chemical Formula 1-1) of the present invention in animal models transplanted with NCI-H460 cells, a kind of NSCLC cells resistant to EGFR-targeted agents.

2) Methods

NCI-H460 (ATCC, HTB-177), derived from NSCLC patients, is an NSCLC cell line having wild-type EGFR and mutant KRAS, which is highly resistant to EGFR TKI (Tarceva®, Iressa®). These cells were used to evaluate in vivo anticancer activity of the compounds of the present invention. In this regard, NCI-H460 cells were cultured on a mass scale, and subcutaneously transplanted at a density of $5 \times 10^6$ cells in 0.2 mL of HBSS per head into the right axillar region of mice (Balb/c nude mice). Three to five days after the transplantation, tumor masses were observed. From Day 6 (D1) to Day 18 (D12) after the transplantation, three groups of the NCI-H460-transplanted mice were administered with compound of Chemical Formula 1-1 or paclitaxel as summarized in Table 3, below.

TABLE 3

| Group | Administered Substance and Amount thereof |
|---|---|
| 1 | Vehicle_Saline |
| 2 | 1-1_150 mg/kg |
| 3 | paclitaxel_20 mg/kg |

As the control, only saline was intravenously injected once a day to reach a total of six injections over a two week period (three times per week, D1, 3, 5, 8, 10, 12) (Group 1).

The compound of Chemical Formula 1-1 was dissolved in saline and intravenously injected at a dose of 150 mg/kg once a day to reach a total of six injections over a two week period (three times per week, D1, 3, 5, 8, 10, 12) (Group 2).

Paclitaxel was intraperitoneally injected at a dose of 20 mg/kg once a day to reach a total of two injections over two weeks (three times per week, D1, 3, 5, 8, 10, 12) (Group 3).

3) Results i. Changes in Body Weight and Tumor Size and Evaluation of Tumor Growth Inhibition (TGI)

Figure 7:
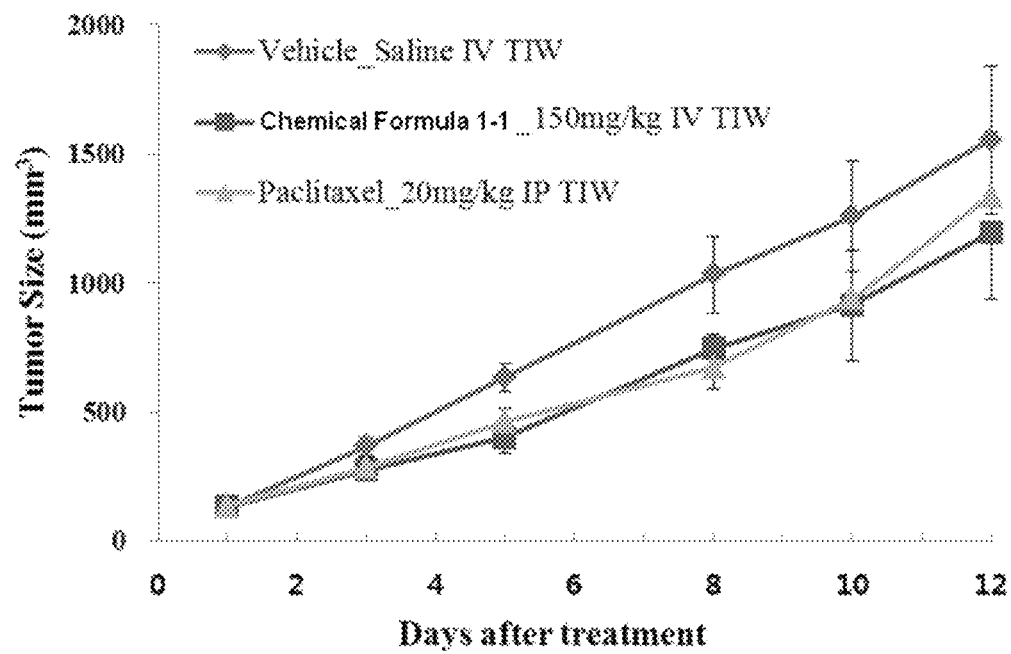
FIG. 7 is a graph in which tumor sizes (vertical axis) of the groups administered with the pyrazino-triazine derivative (Chemical Formula 1-1) are plotted against the days after treatment (horizontal axis)
Figure 8:
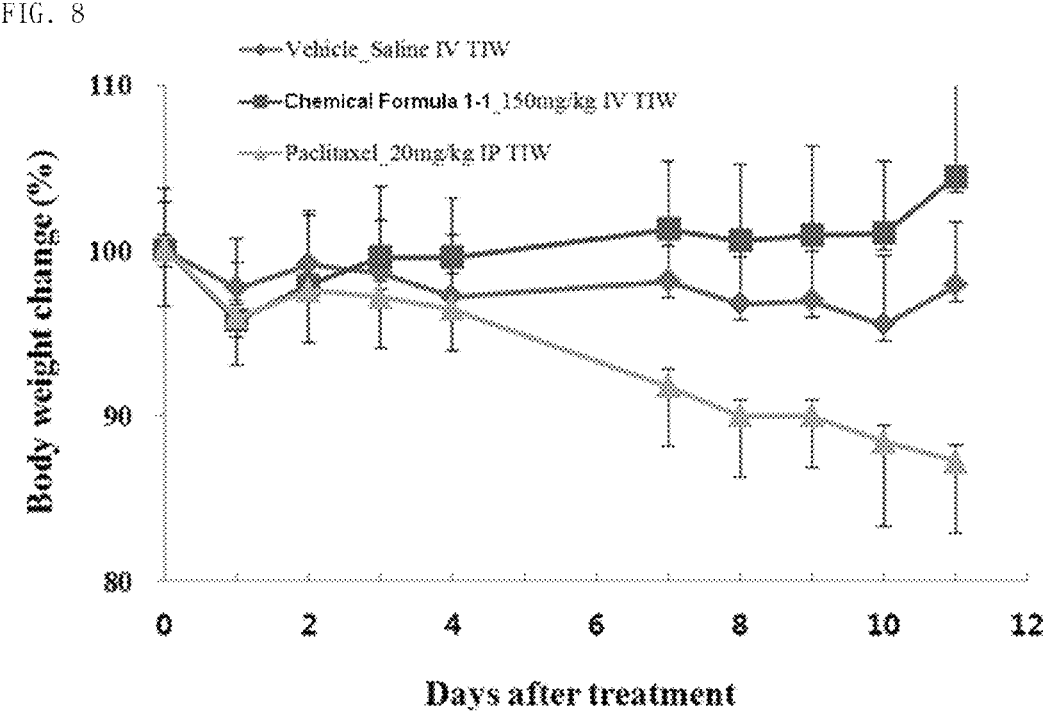
FIG. 8 is a graph in which body weights (vertical axis) of the groups administered with the pyrazino-triazine derivative (Chemical Formula 1-1) are plotted against the days after treatment (horizontal axis).

Body weights and tumor sizes of the mice were measured in the same manner as in EXPERIMENTAL Example 1 and tumor growth inhibition (TGI, %) was also calculated. The mean volume of tumors before experiment (mean starting tumor volume) was 136 $mm^3$ Measurements are summarized in Table 4 and depicted in FIGS. 7 and 8.

ii. Mortality and Maximum Body Weight Loss (MBL)

Mortality and MBL were evaluated in the same manner as in EXPERIMENTAL Example 1, and the results are summarized in Table 4, below.

TABLE 4

| Group | Mortality | Tumor size @D 12 (Mean ± S.E. $mm^3$) | TGI % D12 | MBL (%) |
|---|---|---|---|---|
| 1 | 0/6 | 1554 ± 285 | — | 4 (@D11) |
| 2 | 0/6 | 1196 ± 247 | 25 | 4 (@D2) |
| 3 | 0/6 | 1339 ± 260 | 15 | 13 (@D12) |

EXPERIMENTAL EXAMPLE 3

Therapeutic Effect of Chemical Formula 1-1 on NSCLC of EGFR TKI-Sensitive Cell (HCC827)

1) Purpose

This experiment aims to evaluate the in vivo anticancer activity of the pyrazino-triazine derivatives (Chemical Formula 1-1) of the present invention in animal models transplanted with HCC827 cells, a kind of NSCLC cells hypersensitive to EGFR-targeted agents.

2) Methods

HCC827 (ATCC, CRL-2868), derived from NSCLC patients, is an NSCLC cell line having a deletion mutation on exon 19 (E746-A750), which is sensitive to EGFR TKI (Tarceva®, Iressa®). These cells were used to evaluate in vivo anticancer activity of the compounds of the present invention. In this regard, HCC827 cells were cultured on a mass scale, and subcutaneously transplanted at a density of $5 \times 10^6$ cells in 0.2 mL of HBSS per head into the right axillar region of mice (Balb/c nude mice). Three to five days after the transplantation, tumor masses were observed. From Day 8 to Day 32 after the transplantation, six groups of the HCC827-transplanted mice were administered with the compound of Chemical Formula 1-1 and/or paclitaxel as summarized in Table 5, below.

TABLE 5

| Group | Administered Substance and Amount thereof |
|---|---|
| 1 | Vehicle_Saline |
| 2 | 1-1_100 mg/kg |
| 3 | 1-1_150 mg/kg |
| 4 | 1-1_100 mg/kg + paclitaxel_10 mg/kg |
| 5 | 1-1_150 mg/kg + paclitaxel_10 mg/kg |
| 6 | paclitaxel_10 mg/kg |

As the control, only saline was intravenously injected once a day to reach a total of 20 injections over a four week period (five times per week, D8-12, D15-19, D22-26, and D29-32) (Group 1).

The compound of Chemical Formula 1-1 was dissolved in saline and intravenously injected at a dose of 100 and 150 mg/kg once a day to reach a total of 20 injections over a four week period (five times per week, D8-12, D15-19, D22-26, and D29-32) (Groups 2 and 3, respectively).

Paclitaxel was intraperitoneally injected at a dose of 10 mg/kg once a day to reach a total of four injections over four weeks (once per week, D8, D15, D22, and D29) (Group 6).

The compound of Chemical Formula 1-1 was injected at a dose of 100 mg/kg and 150 mg/kg to the mice administered with paclitaxel at a dose of 10 mg/kg in the same manner as described above (Groups 4 and 5).

3) Results i. Changes in Body Weight and Tumor Size and Evaluation of Tumor Growth Inhibition (TGI)

Figure 9:
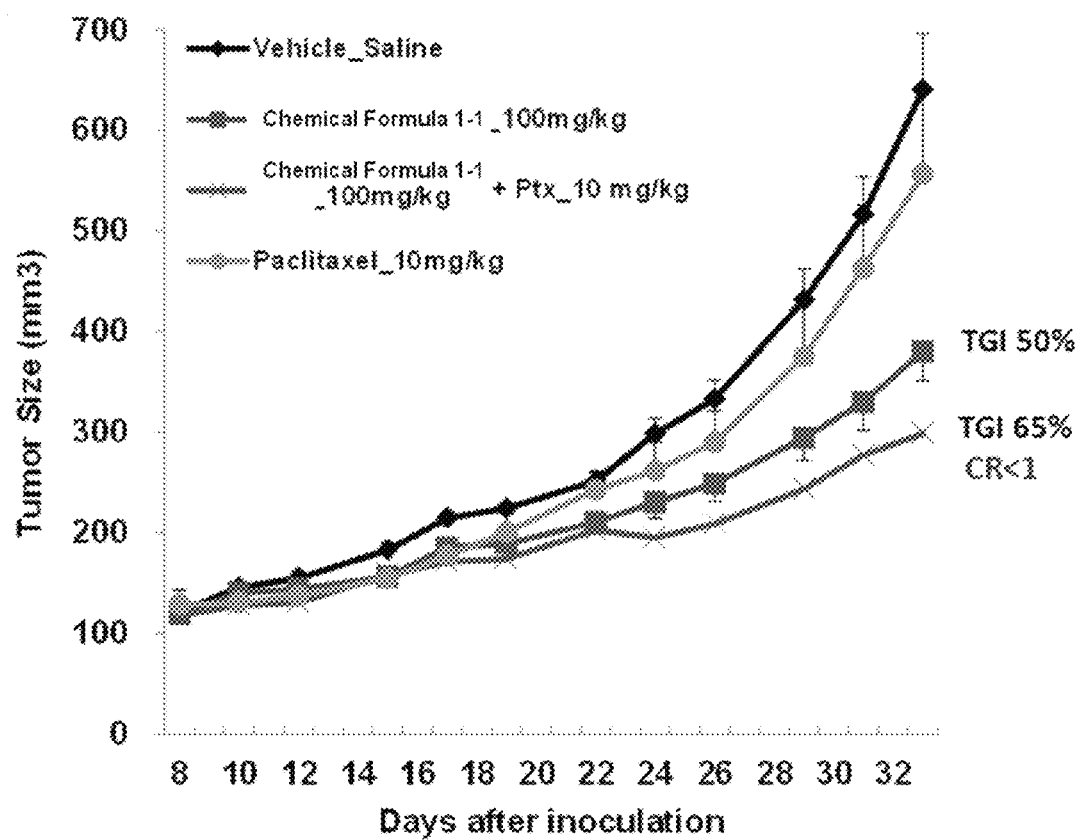
FIG. 9 is a graph in which tumor sizes (vertical axis) of the groups administered with the pyrazino-triazine derivative (Chemical Formula 1-1) are plotted against the days after inoculation (horizontal axis)
Figure 10:
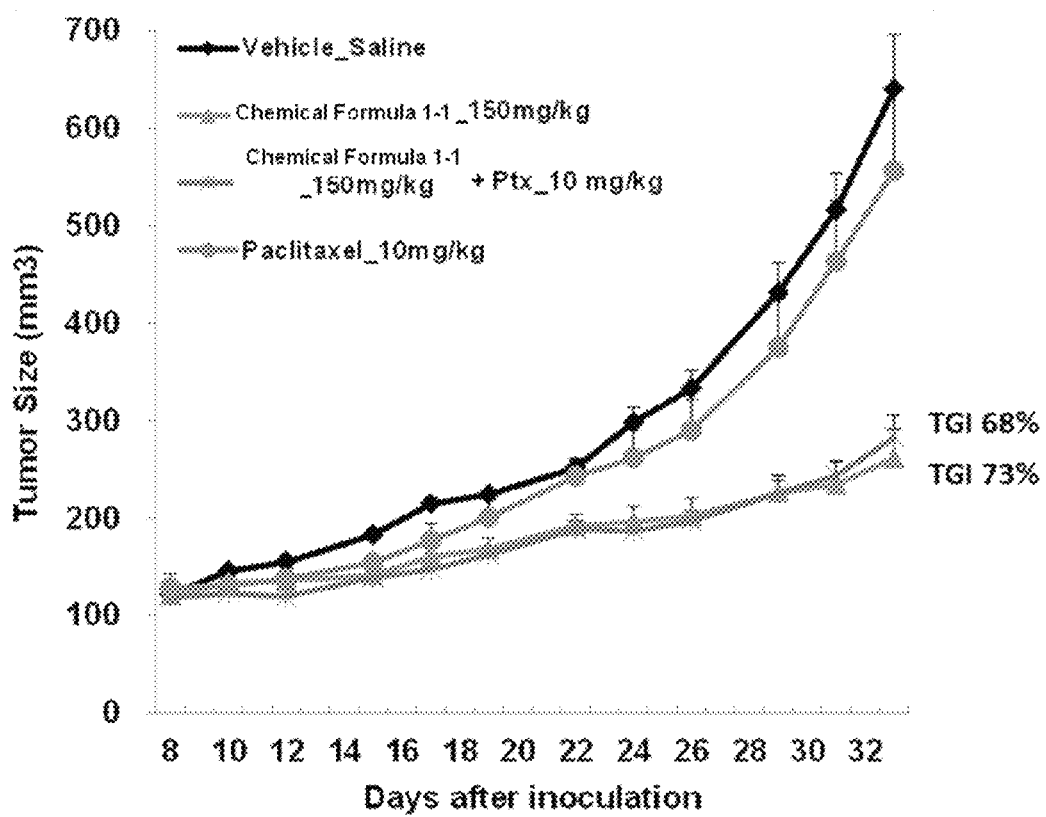
FIG. 10 is a graph in which tumor sizes (vertical axis) of the groups administered with the pyrazino-triazine derivative (Chemical Formula 1-1) are plotted against the days after inoculation (horizontal axis)

Body weights and tumor sizes of the mice were measured in the same manner as in EXPERIMENTAL Example 1 and tumor growth inhibition (TGI, %) was also calculated. The mean volume of tumors before experiment (mean starting tumor volume) was 121 mm$^3$ Measurements are summarized in Table 6 and depicted in FIGS. 9 and 10.

ii. Mortality and Maximum Body Weight Loss (MBL)

Mortality and MBL were evaluated in the same manner as in EXPERIMENTAL Example 1, and the results are summarized in Table 6, below.

TABLE 6

| Group | Mortality | Tumor size @D 33 (Mean ± S.E. mm$^3$) | TGI % D33 | MBL (%) |
|---|---|---|---|---|
| 1 | 0/7 | 641 ± 56 | | 1 (D11) |
| 2 | 0/7 | 380 ± 29 | 50 | 1 (D11) |
| 3 | 0/7 | 262 ± 30 | 68 | 1 (D11) |
| 4 | 0/7 | 299 ± 63 | 65 | 1 (D11) |
| 5 | 0/7 | 283 ± 23 | 73 | 5 (D11) |
| 6 | 0/6 | 557 ± 83 | 18 | 2 (D11) |

The therapeutic effects of compound 1-1 on various NSCLC cell lines, evaluated in EXPERIMENTAL Examples 1 to 3, are summarized in terms of tumor growth inhibition (TGI) in Table 7, below.

TABLE 7

| NSCLC cell line | Cpd 1-1 TGI % | | 1' Agent Paclitaxel TGI % | Combination TGI % |
|---|---|---|---|---|
| NCI-H1975 (EGFR TKI resistant) | 100% | > | 30% | 171% (Synergism) |
| HCC827 (EGFR TKI sensitive) | 78% | > | 18% | 68% |

TABLE 7-continued

| NSCLC cell line | Cpd 1-1 TGI % | | 1' Agent Paclitaxel TGI % | Combination TGI % |
|---|---|---|---|---|
| NCI-H460 (EGFR TKI resistant) | 25% (TIW) | > | 15% | NT |

The compound of Chemical Formula 1-1 exhibited higher anticancer activity in animal models transplanted with NSCLC cell lines, compared to the standard agent paclitaxel, with a peak of inhibitory activity against NCI-H1975 having EGFR T790M mutation, which is causative of resistance to EFGR TKI and a synergistic peak with paclitaxel against NCI-H1975, demonstrating itself as a potential therapeutic agent for patients with EGFR TKI-resistant NSCLC.

EXPERIMENTAL EXAMPLE 4

In vitro Anticancer Activity of Compound 1-1P Against Various NSCLC Cell Lines

1) Purpose

This experiment aims to evaluate the in vitro anticancer activity of the pyrazino-triazine derivative (Chemical Formula 1-1P) of the present invention in various NSCLC cell lines.

2) Methods

NSCLC cells lines were seeded at a density of 5×10$^3$ cells/well into 96-well plates. Compound 1-1P and the reference drug doxorubicin were serially diluted by ½ in the concentration range of from 0.001 μM to 1 μM and the cells in each well were treated with each dilution in duplicate, followed by incubation for 72 hours in a 37° C., 5% CO$_2$ incubator. Cell-Titer-Glo® (Luminescent Cell Viability Assay, #G7573, Promega) was added in an amount of 100 μL to each well and shaken for 2 min to lyze the cells. After incubation for 10 min at room temperature (25° C.), luminescence from each well was on a luminometer (Envision (Perkinelmer).

3) Results

The anticancer activity depending on the administration of Compound 1-1P was evaluated over seven different NSCLC cell lines by cell growth inhibition 50 (GI$_{50}$), a concentration needed to reduce the growth of treated cells to half that of untreated cells, calculated according to the following formula. The results are summarized in Table 8.

$$GI_{50}=(50-(y_1-((y_1-y_2)/(x_1-x_2))*x_1)/((y_1-y_2)/(x_1-x_2))$$

$x_1$, $x_2$=50% cell kill or lethal concentrations $y_1$, $y_2$=cell densities at 50% cell kill or lethal concentrations

TABLE 8

| Cancer type | Cell line | GI$_{50}$, nM, 72 hrs Cpd 1-1P |
|---|---|---|
| Lung | NCI-H23 | 67 |
| | NCI-H1650 | 156 |
| | NCI-H1975 | 111 |
| | HCC827 | 115 |
| | NCI-H460 | 272 |
| | A549 | 372 |
| | PC6 | 493 |

NCI-H460, NCI-H23 and A549 cells, which are NSCLC cells lines having wild-type EGFR and mutant KRAS, were 50% growth halted with 272, 67 and 372 nM of the compound, respectively.

HCC827 is an NSCLC cell line which has a deletion mutation on EGFR exon 19 (E746-A750) and a mutant KRAS gene and is hyper-sensitive to EGFR TKI. Compound 1-1P was found to have a $GI_{50}$ of 115 nM against HCC827.

NCI-H1650 is an NSCLC cell line which has a deletion mutation on EGFR exon 19 (E746-A750) and a KRAS mutation and is resistant to EGFR TKI. Compound 1-1P was found to have a $GI_{50}$ of 156 nM against NCI-H1650.

NCI-H1975 is an NSCLC cell line which has a T790M mutation and is resistant to EGFR TKI. Its growth was 50% halted at a concentration of 111 nM of Compound 1-1P.

EXPERIMENTAL EXAMPLE 5

Therapeutic Effect of Bisodium Salt of Compound 2-2 on NSCLC of EGFR TKI Resistant Cells (NCI-H1975)

1) Purpose

This experiment aims to evaluate the in vivo anticancer activity of the pyrazino-triazine derivative (bisodium salt of Chemical Formula 2-2) of the present invention in animal models transplanted with NCI-H1975 cells, a kind of NSCLC cell resistant to EGFR-targeted agents.

2) Methods

NCI-H1975 (ATCC, CRL-5908), derived from NSCLC patients, is an NSCLC cell line having a double mutation of EGFR L858R and T790M, which is hyper-resistant to EGFR TKI (Tarceva®, Iressa®). These cells were used to evaluate the in vivo anticancer activity of the compounds of the present invention. In this context, NCI-H1975 cells were cultured on a mass scale, and subcutaneously transplanted at a density of $5 \times 10^6$ cells in 0.2 mL of HBSS per head into the right axillar region of mice (Balb/c nude mice). Three to five days after the transplantation, tumor masses were observed. From Day 11 (D11) to Day 22 (D22) after the transplantation, three groups of the NCI-H1975-transplanted mice were administered with a bisodium salt of the compound of Chemical Formula 2-2 or cisplatin as summarized in Table 9, below.

TABLE 9

| Group | Administered Material | Dose (mg/kg) | ROA | Dosing |
|---|---|---|---|---|
| 1 | Vehicle | — | IV | QDx5 for 2 weeks |
| 2 | 2Na Salt of Cpd. 2-2 | 200 | IV | QDx5 for 2 weeks |
| 3 | Cisplatin | 2.5 | IV | BIW for 2 weeks |

3) Results i. Changes in Body Weight and Tumor Size and Evaluation of Tumor Growth Inhibition (TGI)

Body weights and tumor sizes of the mice were measured in the same manner as in EXPERIMENTAL Example 1 and tumor growth inhibition (TGI, %) was also calculated. The mean volume of tumors before the experiment (mean starting tumor volume) was 118 mm³ ii. Mortality and Maximum Body Weight Loss (MBL)

Figure 11:
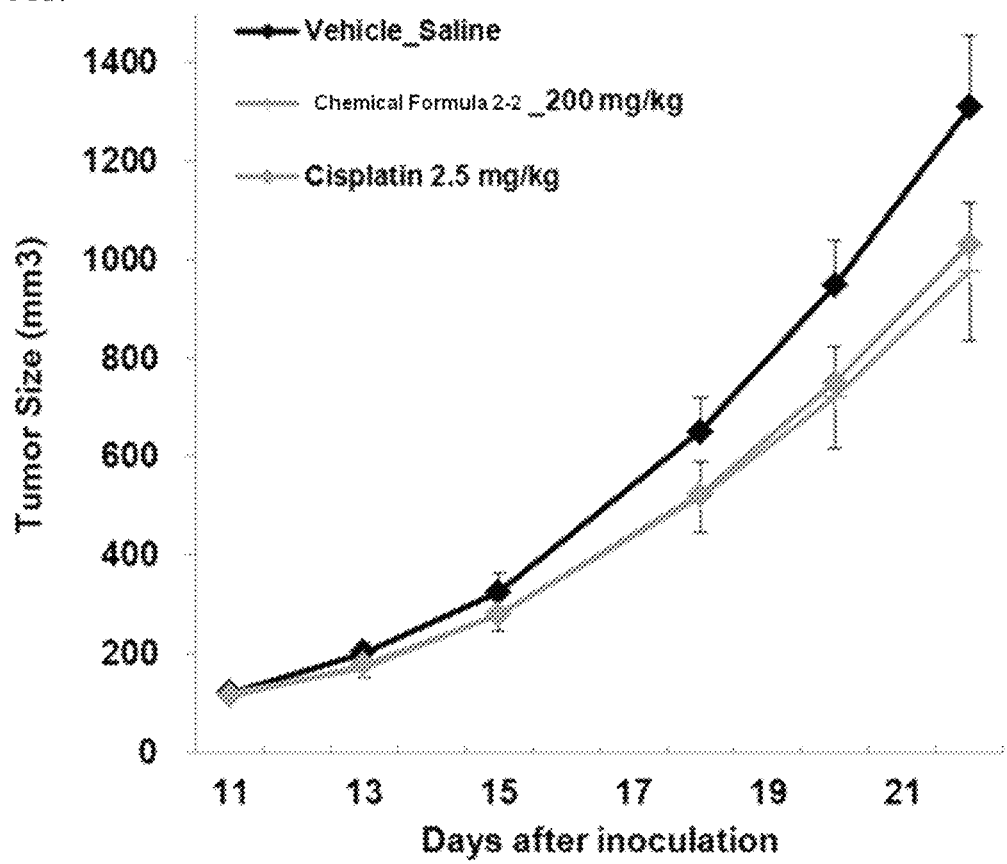
FIG. 11 is a graph in which tumor sizes (vertical axis) of the groups administered with the pyrazino-triazine derivative (bisodium salt of Chemical Formula 2-2) are plotted against the days after inoculation (horizontal axis)
Figure 12:
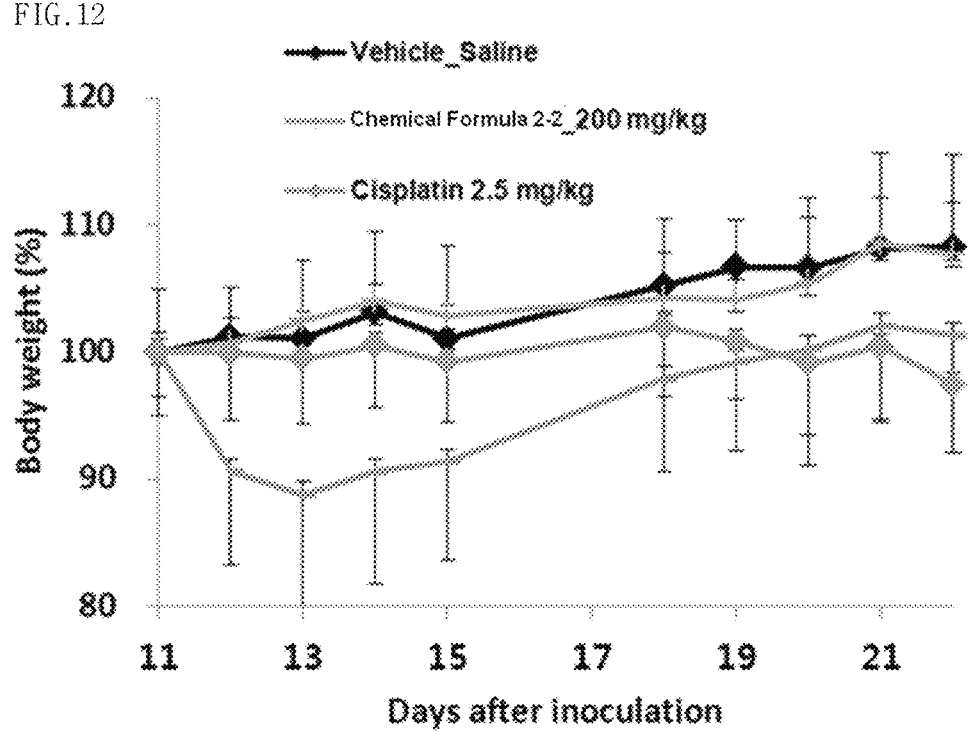
FIG. 12 is a graph in which body weights (vertical axis) of the groups administered with the pyrazino-triazine derivative (bisodium salt of Chemical Formula 2-2) are plotted against the days after treatment (horizontal axis)

Mortality and MBL were evaluated in the same manner as in EXPERIMENTAL Example 1, and the results are summarized in Table 10 and depicted in FIGS. 11 and 12.

TABLE 10

| Group | Mortality | Tumor size @D 22 (Mean ± S.E. mm³) | TGI % D22 | MBL (%) |
|---|---|---|---|---|
| 1 | 0/7 | 947 ± 92 | | no loss |
| 2 | 0/6 | 720 ± 104 | 27 | no loss |
| 3 | 0/6 | 750 ± 53 | 23 | 1 (D20) |

EXPERIMENTAL EXAMPLE 6

Therapeutic Effect of Compounds 1-3 and 1-5 on NSCLC of EGFR TKI Resistant Cells (NCI-H1975)

1) Purpose

This experiment aims to evaluate the in vivo anticancer activity of the pyrazino-triazine derivatives (compounds 1-3 and 1-5) of the present invention in animal models transplanted with NCI-H1975 cells, a kind of NSCLC cell resistant to EGFR-targeted agents.

2) Methods

NCI-H1975 (ATCC, CRL-5908), derived from NSCLC patients, is an NSCLC cell line having a double mutation of EGFR L858R and T790M, which is hyper-resistant to EGFR TKI (Tarceva®, Iressa®). These cells were used to evaluate in vivo anticancer activity of the compounds of the present invention. In this context, NCI-H1975 cells were cultured on a mass scale, and subcutaneously transplanted at a density of $5 \times 10^6$ cells in 0.2 mL of HBSS per head into the right axillar region of mice (Balb/c nude mice). Three to five days after the transplantation, tumor masses were observed. From Day 11 (D11) to Day 22 (D22) after the transplantation, five groups of the NCI-H1975-transplanted mice were administered with compounds 1-3 and 1-5 as summarized in Table 11, below.

TABLE 11

| Group | Administered material | Dose (mg/kg) | ROA | Dosing |
|---|---|---|---|---|
| 1 | Vehicle | — | IV | QDx5 |
| 2 | Cpd. 1-3 | 40 | IV | for |
| 3 | Cpd. 1-5 | 30 | IV | 2 weeks |

3) Results i. Changes in Body Weight and Tumor Size and Evaluation of Tumor Growth Inhibition (TGI)

Body weights and tumor sizes of the mice were measured in the same manner as in EXPERIMENTAL Example 1 and tumor growth inhibition (TGI, %) was also calculated. The mean volume of tumors before experiment (mean starting tumor volume) was 142 mm³ ii. Mortality and Maximum Body weight Loss (MBL)

Figure 13:
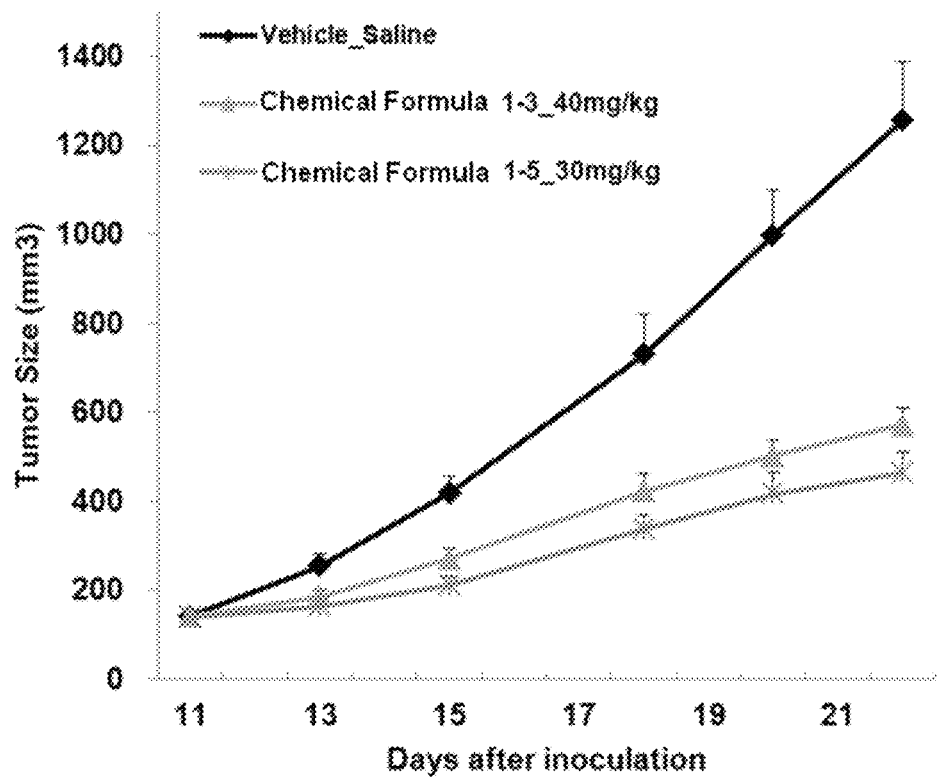
FIG. 13 is a graph in which tumor sizes (vertical axis) of the groups administered with the pyrazino-triazine derivatives (Chemical Formulas 1-3 and 1-5) are plotted against the days after inoculation (horizontal axis)
Figure 14:
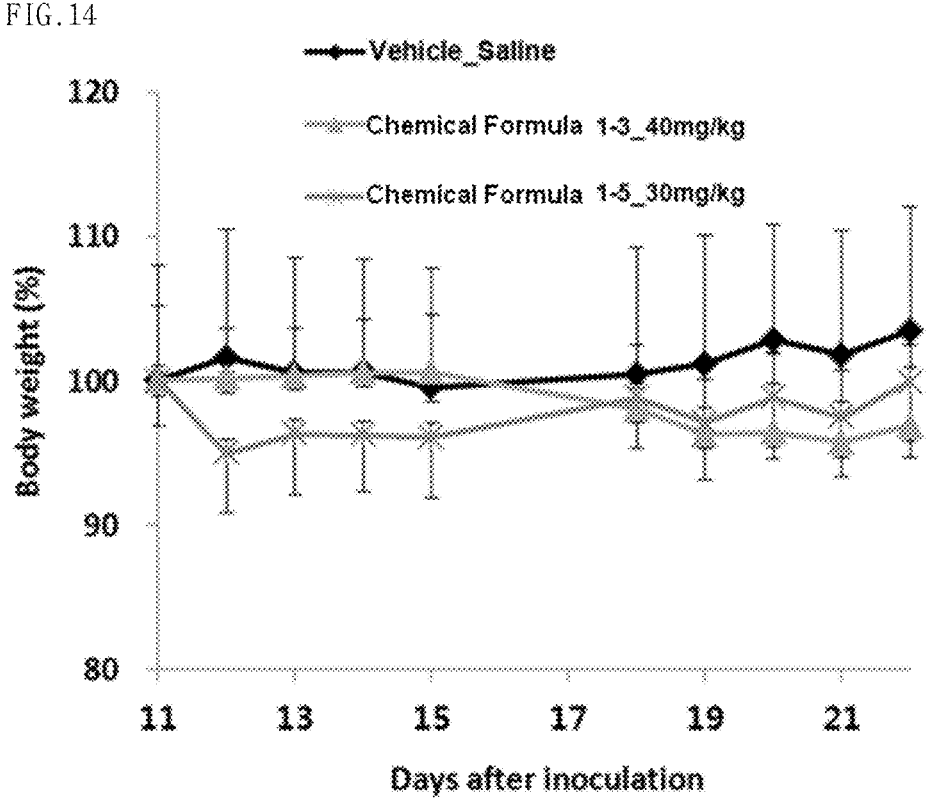
FIG. 14 is a graph in which body weights (vertical axis) of the groups administered with the pyrazino-triazine derivative (Chemical Formulas 1-3 and 1-5) are plotted against the days after treatment (horizontal axis)

Mortality and MBL were evaluated in the same manner as in EXPERIMENTAL Example 1, and the results are summarized in Table 12 and depicted in FIGS. 13 and 14.

TABLE 12

| Group | Mortality | Tumor size @D 22 (Mean ± S.E. mm³) | TGI % D22 | MBL (%) |
|---|---|---|---|---|
| 1 | 0/6 | 1255 ± 133 | | no loss |
| 2 | 0/6 | 571 ± 38 | 62 | 4 (D19) |
| 3 | 0/6 | 464 ± 45 | 71 | 5 (D12) |

EXPERIMENTAL EXAMPLE 8

Therapeutic Effect of Compounds 1-7 on NSCLC of EGFR TKI Resistant Cells (NCI-H1975)

1) Purpose

This experiment aims to evaluate the in vivo anticancer activity of the pyrazino-triazine derivative (compound 1-7) of the present invention in animal models transplanted with NCI-H1975 cells, a kind of NSCLC cells resistant to EGFR-targeted agents.

2) Methods

NCI-H1975 (ATCC, CRL-5908), derived from NSCLC patients, is an NSCLC cell line having a double mutation of EGFR L858R and T790M, which is hyper-resistant to EGFR TKI (Tarceva®, Iressa®). These cells were used to evaluate in vivo anticancer activity of the compounds of the present invention. In this context, NCI-H1975 cells were cultured on a mass scale, and subcutaneously transplanted at a density of $5 \times 10^6$ cells in 0.2 mL of HBSS per head into the right axillar region of mice (Balb/c nude mice). Three to five days after the transplantation, tumor masses were observed. From Day 11 (D11) to Day 22 (D22) after the transplantation, two groups of the NCI-H1975-transplanted mice were administered with compound 1-7 as summarized in Table 13, below.

TABLE 13

| Group | Administered material | Dose (mg/kg) | ROA | Dosing |
|---|---|---|---|---|
| 1 | Vehicle | — | IV | BIW for 2 weeks |
| 2 | Cpd. 1-7 | 60 | IV | BIW for 2 weeks |

3) Results i. Changes in Body Weight and Tumor Size and Evaluation of Tumor Growth Inhibition (TGI)

Body weights and tumor sizes of the mice were measured in the same manner as in EXPERIMENTAL Example 1 and tumor growth inhibition (TGI, %) was also calculated. The mean volume of tumors before experiment (mean starting tumor volume) was 86 mm³.

ii. Mortality

Figure 15:
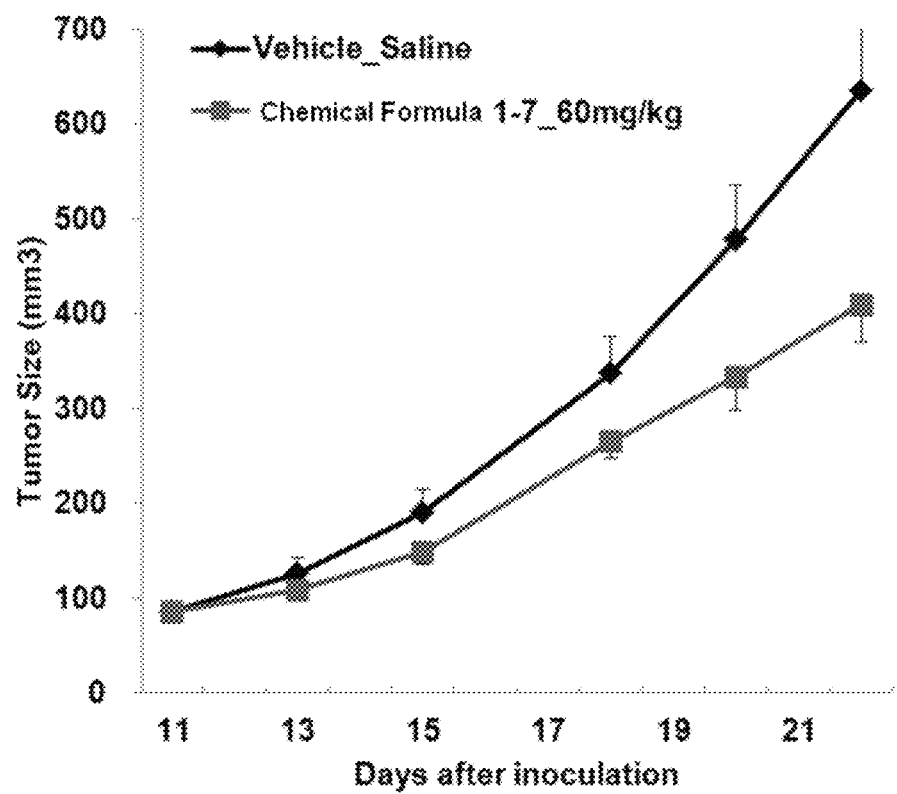
FIG. 15 is a graph in which tumor sizes (vertical axis) of the groups administered with the pyrazino-triazine derivative (Chemical Formula 1-7) are plotted against the days after inoculation (horizontal axis).

Mortality was evaluated in the same manner as in EXPERIMENTAL Example 1, and the results are summarized in Table 14 and depicted in FIG. 15.

TABLE 14

| Group | Mortality | Tumor size @D 22 (Mean ± S.E. mm³) | TGI % D22 |
|---|---|---|---|
| 1 | 0/5 | 635 mm | |
| 2 | 0/5 | 410 mm | 41 |

Industrial Applicability

As described hitherto, the pyrazino-triazine derivatives of the present invention effectively inhibit the growth of various cell lines involved in NSCLC (non-small cell lung cancer) in vitro and in vivo, and thus are suitable for use as agents for the therapy and prophylaxis of NSCLC.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method for treating non-small cell lung cancer (NSCLC), comprising administering to a subject in need thereof a therapeutically effective amount of a compound represented by following Chemical Formulas 1-1 or 1-1P, an isomer thereof, and a pharmaceutically acceptable salt thereof:

[Chemical Formula 1-1]

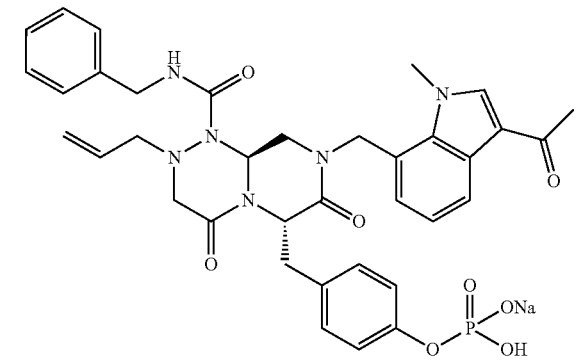

[Chemical Formula 1-1P]

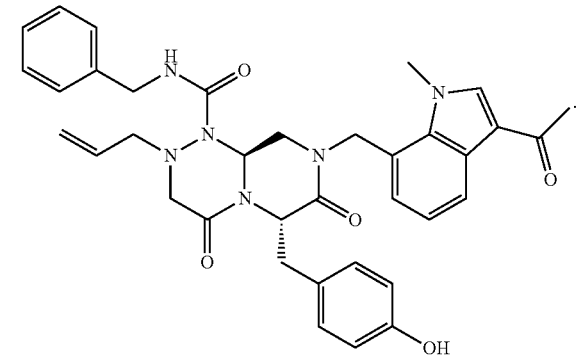

2. A method for treating non-small cell lung cancer (NSCLC), comprising administering to a subject in need thereof a therapeutically effective amount of a compound represented by one of the following Chemical Formulas 1-2 to 1-7, an isomer thereof, and a pharmaceutically acceptable salt thereof:

| No. | Chemical Formula |
|---|---|
| 1-2 | 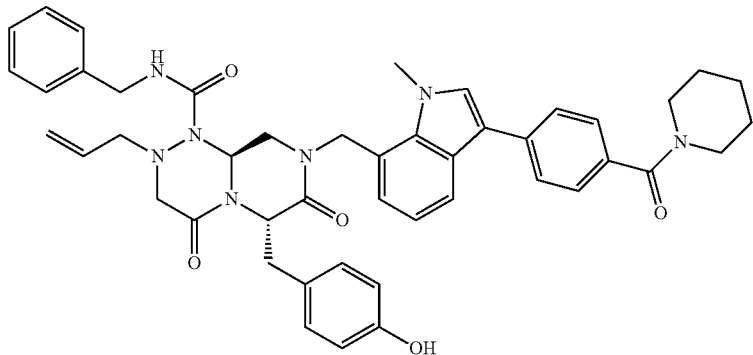 [SMILES: C=CCN1CC(=O)N2[C@@H](Cc3ccc(O)cc3)C(=O)N(Cc3cccc4c(-c5ccc(C(=O)N6CCCCC6)cc5)cn(C)c34)C[C@@H]2N1C(=O)NCc1ccccc1] |
| 1-3 | 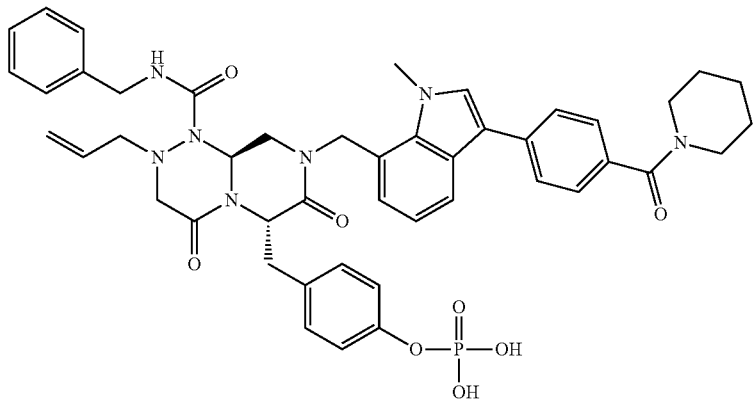 [SMILES: C=CCN1CC(=O)N2[C@@H](Cc3ccc(OP(=O)(O)O)cc3)C(=O)N(Cc3cccc4c(-c5ccc(C(=O)N6CCCCC6)cc5)cn(C)c34)C[C@@H]2N1C(=O)NCc1ccccc1] |
| 1-4 | 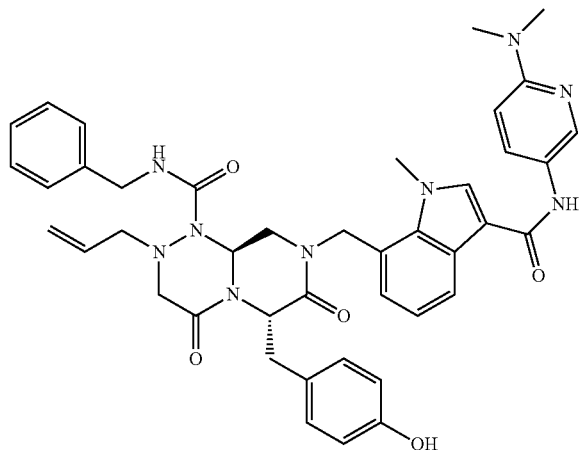 [SMILES: C=CCN1CC(=O)N2[C@@H](Cc3ccc(O)cc3)C(=O)N(Cc3cccc4c(C(=O)Nc5ccc(N(C)C)nc5)cn(C)c34)C[C@@H]2N1C(=O)NCc1ccccc1] |

| No. | Chemical Formula |
|---|---|
| 1-5 | 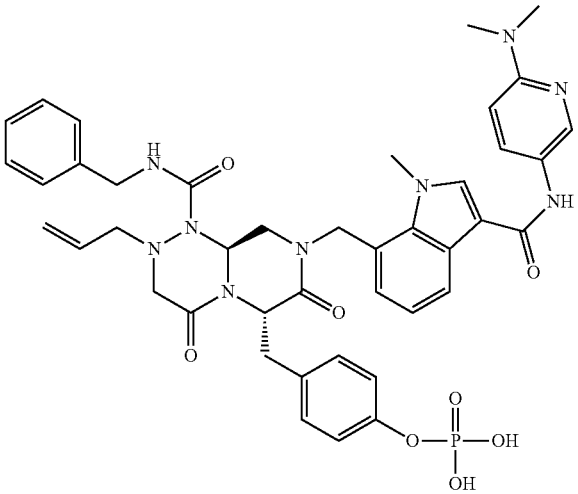 [SMILES: C=CCN1CC(=O)N2[C@@H](Cc3ccc(OP(=O)(O)O)cc3)C(=O)N(Cc3cccc4c(C(=O)Nc5ccc(N(C)C)nc5)cn(C)c34)C[C@@H]2N1C(=O)NCc1ccccc1] |
| 1-6 | 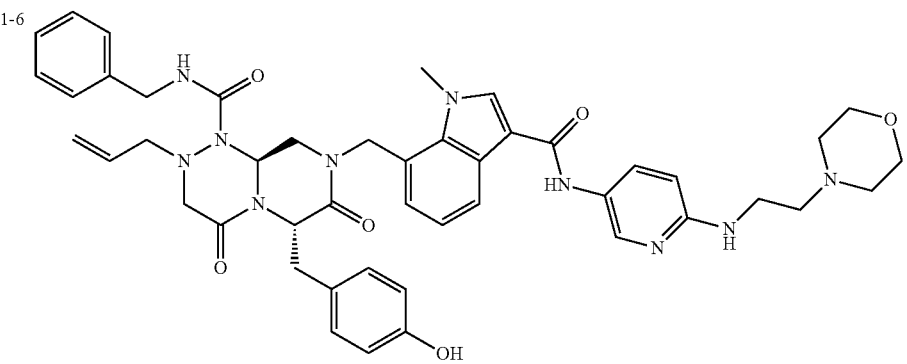 |
| 1-7 | 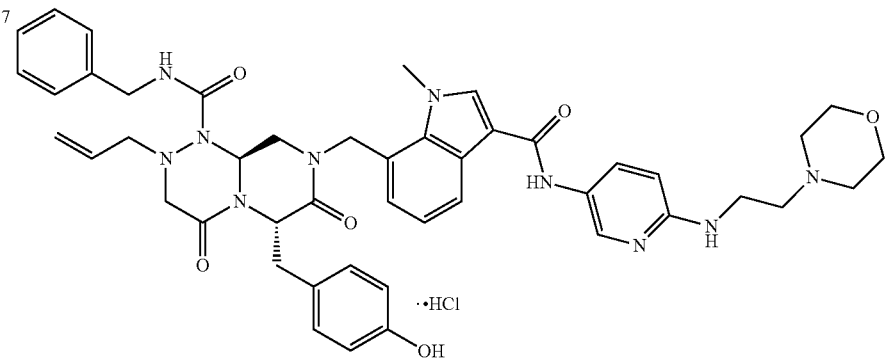 |

3. The method of claim 1, wherein the NSCLC is cancer occurring in a patient having wild-type EGFR (epithelial growth factor receptor) or an active mutation on EGFR.

4. The method of claim 1, wherein the NSCLC is EGFR TKI (Epidermal Growth Factor Receptor tyrosine kinase inhibitor)-resistant cancer.

5. The method of claim 4, wherein the EGFR TKI-resistant cancer is cancer occurring in a patient having mutant EGFR.

6. The method of claim 5, wherein the mutant EGFR has a double mutation of L858R and T790M.

7. The method of claim 1, further comprising:
administering to the subject one or more additional anticancer drugs.

8. The method of claim 7, wherein the one or more additional anticancer drugs comprise paclitaxel.

* * * * *